US007741275B2

(12) United States Patent
Ståhle et al.

(10) Patent No.: US 7,741,275 B2
(45) Date of Patent: Jun. 22, 2010

(54) AGENTS AND USE THEREOF

(75) Inventors: Mona Ståhle, Stockholm (SE); Johan Heilborn, Stockholm (SE); Margareta Frohm Nilsson, Stocksund (SE); Gunter Weber, Solna (SE)

(73) Assignee: Lipopeptide AB, Stockholm (SE)

( * ) Notice: Subject to any disclaimer, the term of this patent is extended or adjusted under 35 U.S.C. 154(b) by 0 days.

(21) Appl. No.: 11/793,708

(22) PCT Filed: Dec. 16, 2005

(86) PCT No.: PCT/GB2005/004900

§ 371 (c)(1),
(2), (4) Date: Oct. 3, 2007

(87) PCT Pub. No.: WO2006/067402

PCT Pub. Date: Jun. 29, 2006

(65) Prior Publication Data

US 2008/0187530 A1    Aug. 7, 2008

Related U.S. Application Data

(60) Provisional application No. 60/637,759, filed on Dec. 22, 2004.

(51) Int. Cl.
*A61K 38/00* (2006.01)
*A61K 39/395* (2006.01)

(52) U.S. Cl. .................................. 514/2; 424/130.1

(58) Field of Classification Search .................. None
See application file for complete search history.

(56) References Cited

U.S. PATENT DOCUMENTS

| 4,816,567 | A | 3/1989 | Cabilly et al. |
| 4,987,071 | A | 1/1991 | Cech et al. |
| 5,093,246 | A | 3/1992 | Cech et al. |
| 5,116,742 | A | 5/1992 | Cech et al. |
| 5,149,796 | A | 9/1992 | Rossi et al. |
| 5,168,053 | A | 12/1992 | Altman et al. |
| 5,180,818 | A | 1/1993 | Cech et al. |
| 5,831,012 | A | 11/1998 | Nilsson et al. |
| 2006/0057134 | A1 | 3/2006 | Kirikae et al. |

FOREIGN PATENT DOCUMENTS

| EP | 1 358 888 A1 | 11/2003 |
| WO | WO-94/10323 A1 | 5/1994 |
| WO | WO-95/20943 A1 | 8/1995 |
| WO | WO-95/20944 A1 | 8/1995 |
| WO | WO-95/20945 A1 | 8/1995 |
| WO | WO-03/106491 A2 | 12/2003 |
| WO | WO-2004/009640 A1 | 1/2004 |
| WO | WO-2004/056307 A | 7/2004 |
| WO | WO-2004/067025 A | 8/2004 |
| WO | WO-2004/098536 A | 11/2004 |

OTHER PUBLICATIONS

Agerberth et al., 1995, *Proc Natl Acad Sci USA* 92:195-199.
Agerberth et al., 2000, *Blood*; 96:3086-3093.
Agrawal et al., 1988, Proc. Natl. Acad. Sci. USA 85:7079-7083.
Agrawal et al., 1989, *Proc. Natl. Acad. Sci. USA* 86:7790-7794.
Agrawal et al., 1990, Proc. Natl. Acad. Sci. USA 87:1401-1405.
Agrawal et al., 1991, *Proc. Natl. Acad. Sci. USA* 88:7595-7599.
Agarwal et al., 1996, *J Biol Chem* 271(21):12209-12212.
Agrawal and Goodchild, 1987, *Tetrahedron Letters* 28(31), 3539-3542.
Agrawal and Tang, 1990, *Tetrahedron Letters* 31, 7541-7544.
Andela and Rosier, 2004, *Molecular Cancer*, 3: 8-19.
Aoki et al., 1997, *Biochem Biophys Res Commun* 231:540-545.
Bals et al., 1998, *J. Clin. Invest.*,102:874-880.
Bals et al., 1998, *Proc Natl Acad Sci USA*, 95:9541-9546.
Bernstein, 2001, *Nature* 409:363-366.
Bischoff et al., 1996, *Science* 274, 373-376.
Boerner et al., 1991. *J. Immunol.* 147:86-95.
Boukamp et al., 1998. *J Cell Biol*;106:761-771.
Braff et al., 2005, *J Immunol* 174:4271-4278.
Brannon-Peppas & Blanchette, 2004, *Adv Drug Deliv Rev.* 56:1649-1659.
Brantl, 2002, *Biochem. Biophys Act.* 1575:15-25.
Burchell et al., 1987, *Cancer Res.* 47, 5476-5482.
Clarke et al., 1985, Proc. Natl. Acad. Sci. USA 82, 1766-1770.
Cole et al., 1984. *Mol. Cell. Biol.* 62:109-120.
Cote et al., 1983. *Proc. Natl. Acad. Sci. USA* 80:2026-2030.
Cosstick and Vyle., 1989, *Tetrahedron Letters* 30(35), 4693-4696.
Cotten et al., 1992, *Proc. Natl. Acad. Sci. USA* 89, 6094-6098.
Cowland et al., 1995, *FEBS Lett.* 368:173-176.
Cullen, 2002, *Nat. Immunol.* 3 by facsimile(7):597-599.
Culver et al., 1992, *Science* 256, 1550-1552.
Dass, 2001, *Drug Deliv.* 8:191-213.
Dass, 2002, *J Pharm Pharmacol.* 54(1):3-27.
Denny, 2004, *Cancer Invest.* 22(4):604-619.
Dorschner et al., 2001, *J Invest Dermatol* 117:91-97.
Fields & Song, 1989, *Nature* 340:245-246.
Fiucci et al., 2002, *Oncogene* 21: 2365-2375.
Frankel et al, 1999, *J Neurosurg* 91:261-267.
Frohm Nilsson et al., 1999, *Infect Immun*;67(5):2561-2566.
Frohm et al., 1996, *Eur. J. Biochem.*; 237; 86-92.
Frohm et al., 1997, *J. Biol. Chem.*; 272(24):15258-15263.
Gudmundsson et al., 1995, *Proc Natl Acad Sci USA* 92:7085-7089.
Gudmundsson et al., 1996, *Eur J Biochem* 238:325-332.
Hammond et al., 2001, *Nat. Rev. Gen.* 2:110-119.

(Continued)

*Primary Examiner*—Christopher H Yaen
(74) *Attorney, Agent, or Firm*—Birch, Stewart, Kolasch & Birch, LLP

(57) ABSTRACT

The present invention provides agents for inhibiting the proliferation of cancer cells, wherein the agent inhibits the biological activity of hCAP18/LL-37. In a preferred embodiment, the agent alters the transcription, translation and/or binding properties of hCAP18/LL-37. Preferably, the agent is selected from the group consisting of short interfering RNA (siRNA) molecules, antisense oligonucleotides and compounds with binding affinity for hCAP18/LL-37. The invention further provides methods for inhibiting the proliferation of cancer cells in a patient, as well as methods and kits for diagnosing cancer.

7 Claims, 14 Drawing Sheets

OTHER PUBLICATIONS

Figure 1:
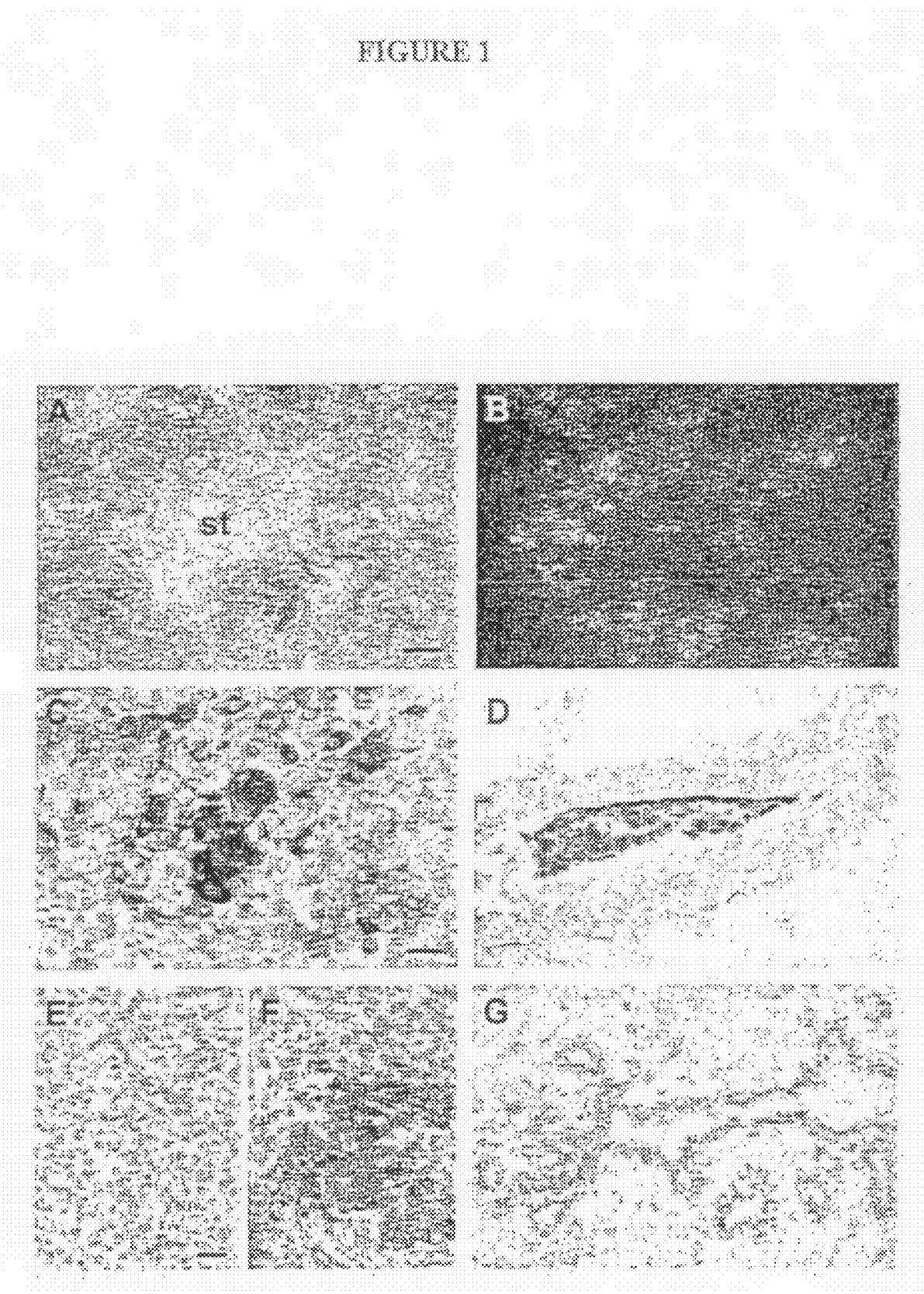

Heilborn et al., 2003, *J Invest Dermatol* 120:379-389.
Hellström et al., 1986 *Cancer Res.* 46, 3917-3923.
Hoogenboom & Winter, 1992, *J. Mol. Biol.* 227:381-388.
Hui et al., 2002, *Anticancer Res*;22:2811-2816.
Hutvagner & Zamore, 2002, *Curr. Opin. Genetics and Development* 12:225-232.
Ishizuka S et al., 2005, *Endocrinology.* 146(4):2023-2030.
Jager et al., 1988, *Biochemistry* 27, 7237-7246.
Jaynes et al., 1989, *Pept Res;* 2(2):157-160.
Jia et al., 2001, *J Pediatr*,138:109-112.
Jones et al., 1986. *Nature* 321:522-525.
Kohler et al., 1975. *Nature* 256:495-497.
Kronenwett et al., 1998, *Blood* 91(3):852-862.
Kuriyama et al., 1991, *Cell Struc. and Func.* 16, 503-510.
Lavigne et al., 1997, *Biochem Biophys Res Commun* 237:566-571.
Lebedeva et al., 2000, *Eur J Pharm Biopharm.* 50:101-119.
Leiter et al., 1990, *Proc. Natl. Acad. Sci. USA* 87, 3430-3434.
Lennon et al., 1996, *Genomics*;33:151-152.
Lu et al., 2005, *Oncogene* 24: 6516-6524.
Ludes-Meyers et al., 2001, *Oncogene* 20:2771-2780.
Luft, 1998, *J Mol Med* 76:75-76.
Lysik & Wu-Pong, 2003, *J Pharm Sci.* 2003 92(8):1559-1573.
Marks et al., 1991, *J. Mol. Biol.* 222:581-597.
Martin & Papahadjopoulos., 1982, *J. Biol. Chem.* 257(1):286-288.
Matveeva et al., 1998, *Nature biotechnology* 16:1374-1375.
Mei et al., 2003, *Breast Cancer Res. and Treatment*, 79:95-105.
Miller & Vile, 1995, *FASEB J.* 9, 190-199.
Mizukawa et al., 2000, *Anticancer Res*;20:2005-2008.
Mizukawa et al. 2001, *Anticancer Res*;21:2171-2174.
Moore et al., 1994, *Pept Res*;7(5):265-269.
Müller et al., 2002, *Am J Pathol*;60(4)1311-24.
Murakami et al., 2002, *J Dent Res*;81(12):845-850.
Murakami et al., 2002, *J Invest Dermatol*;119:1090-1095.
Nässander et al., 1992, *Cancer Res.* 52, 646-653.
Niyonsaba et al., 2002, *Immunology*;106:20-26.
Ohtake et al., 1999, *Br J Cancer* 181(3):393-403.
Orlandi. et al, 1989, *Proc. Natl. Acad. Sci. USA*; 86:3833-3837.
Oren et al., 1999, *Biochem J* 341:501-513.
Plant et al., 1995, *Analyt Biochem* 226: 342-348.
Presta, 1992, *Curr. Op. Struct. Biol.* 2:593-596.
Rajur et al., 1997, *Bioconjug Chem* 8:935-940.
Ramanathan et al., 2002, *Microbes Infect* 4, 361-372.
Riechmann et al., 1988, *Nature* 332:323-327.
Roh et al., 2000, *Oncogene*,19:6138-6143.
Rooseboom et al., 2004, *Pharmacol Rev.* 56(1):53-102.
Sahasrabudhe et al., *J Dent Res* 2000;79(9):1669-74.
Sarin et al., 1988, *Proc. Natl. Acad. Sci. USA* 85, 7448-7451.
Sawaki et al., 2002, *Anticancer Res*;22:2103-2108.
Senter et al., 1988, *Proc. Natl. Acad. Sci. USA* 85, 4842-4846.
Senter et al., 1993, *Bioconjugate*, 4, 3-9.
Sharma, 1993, *Oncogene*;8:939-947.
Sharp, 2001, *Genes. Dev.* 15:485-490.
Shaw et al., 1991, *Nucleic Acids Res.* 19(4):747-750.
Shaykhiev et al., 2005, *Am J Physiol Lung Cell Mol Physiol* 289(5), L842-L848.
Sørensen et al., 1997, *Blood*, 90(7):2796-2803.
Sørensen et al., 1999, *J. Biol. Chem.*, 274(32):22445-22451.
Sørensen et al., 2001, *Blood*, 97(12):3951-3959.
Svensson et al., 1992, *Bioconjugate Chem.* 3, 176-181.
Tang et.al., 1993, *Nucl. Acids Res.* 21, 2729-2735.
Thompson et al., 1994, *Nuc. Acid Res.* 22(22):4673-4680.
Tjabringa et al., 2003, *J Immunol*;171:6690-6696.
Toell et al., 2001, *Mol Pharmacol* 59:1478-1485.
Tokumaru et al., 2005, *J. lmmuinol.*, 175:4662-4668.
Tunzi et al., 2000, *Pediatr Res* 2000; 48(1):30-35.
Uno et al., 2001, *Cancer Res* 61:7855-7860.
Uznanski et al., 1987, *Tetrahedron Letters* 28(29), 3401-3404.
Verhoeyen et al., 1988, *Science* 239:1534-1536.
Walton et al., 1999, *Biotechnol Bioeng* 65:1-9.
Wang Y, et al. 2005, *Breast Cancer Res* 7: R220-R228.
Wagner et al., 1990, *Proc. Natl. Acad. Sci. USA* 87, 3410-3414.
Warburton et al., 2004, *Clin Cancer Res.* 10:2512-2524.
Weber et al., 2005, *J Invest Dermatol.* 124:1080-1082.
Winder et al., 1998, *Biochem Biophys Res Commun* 242:608-612.
Winter et al., 1991, *Nature* 349:293-299.
Witters et al., 1999, *Breast Cancer Res Treat* 53:41-50.
Zanetti et al., 1995, *FEBS Lett* 374:1-5.
Zasloff, 2002, *Nature* 415:389-395.
Zhang et al., 2005, *Genet Vaccines Ther.* 3:5-16.
Zhao & Lee, 2004, *Adv Drug Deliv Rev.* 56(8):1193-1204.
M. Frohm Nilsson, The human antimicrobial peptide hCAP18 in epithelial defense, Thesis (abstract) 43-45, Department of Dermatology, Karolinska Hospital, Karolinska Institut, Stockholm, Sweden, 2001.
Okumura Kazuhiko et al., Cancer Letters, Aug. 30, 2004, vol. 212, No. 2, pp. 185-194, ISR.
Koczulla R et al., Journal of Clinical Investigation, New York, US, vol. 111, No. 11, Jun. 2003, pp. 1665-1672, ISR.
Yang D et al., Journal of Experimental Medicine, Tokyo, JP, vol. 192, No. 7, Oct. 2, 2000, pp. 1069-1074, ISR.
Yang Y-H et al., Leukemia Research, New York, NY, US, vol. 27, No. 10, Oct. 2003, pp. 947-950, ISR.
Heilborn Johan D et al., International Journal of Cancer. May 1, 2005, vol. 114, No. 5, pp. 713-719, ISR.
Al L L et al., Leukemia Research New York, NY, US, vol. 29, No. 5, May 2005, pp. 535-543, ISR.

Figure 5:
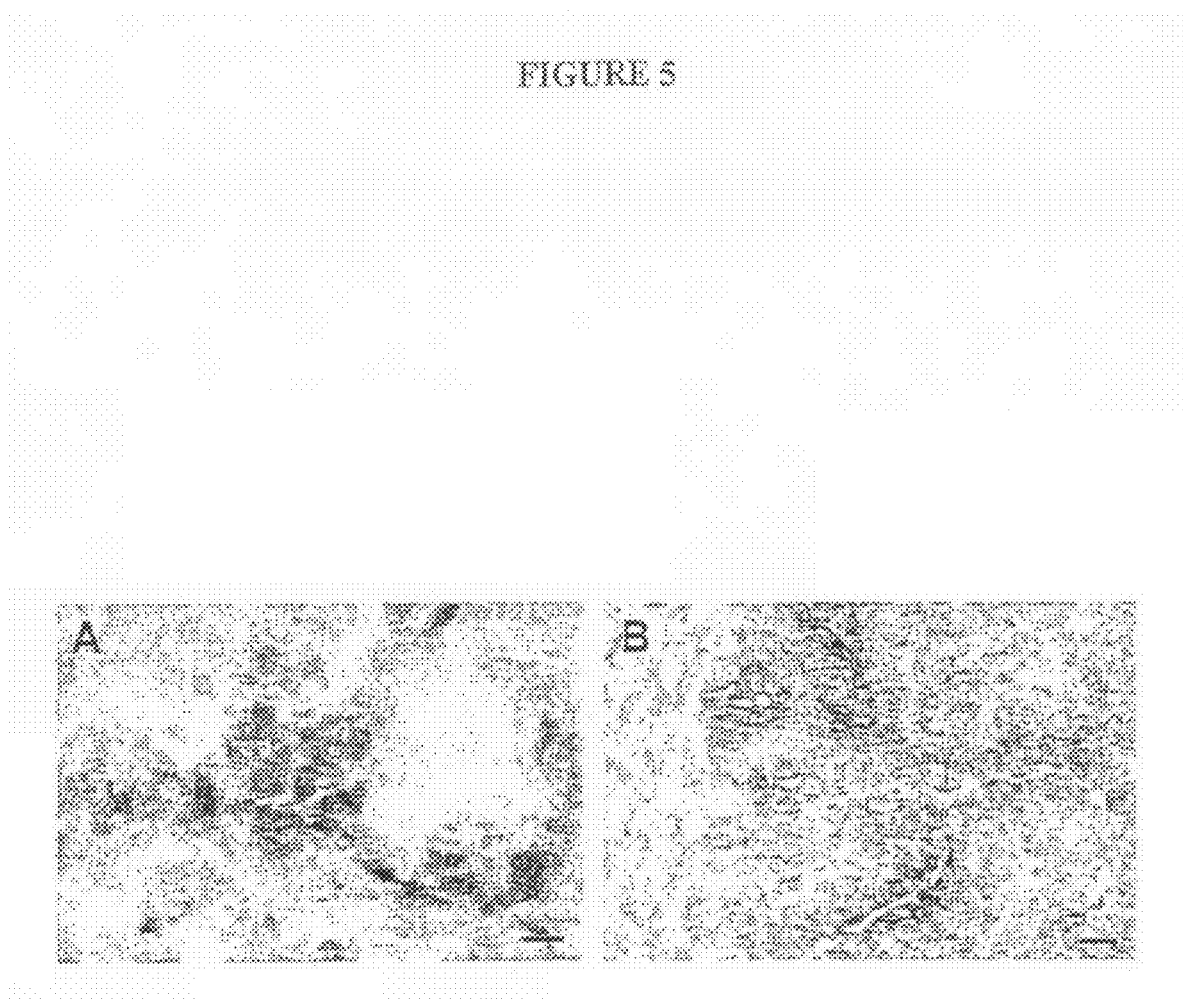

FIGURE 5 - *continued*
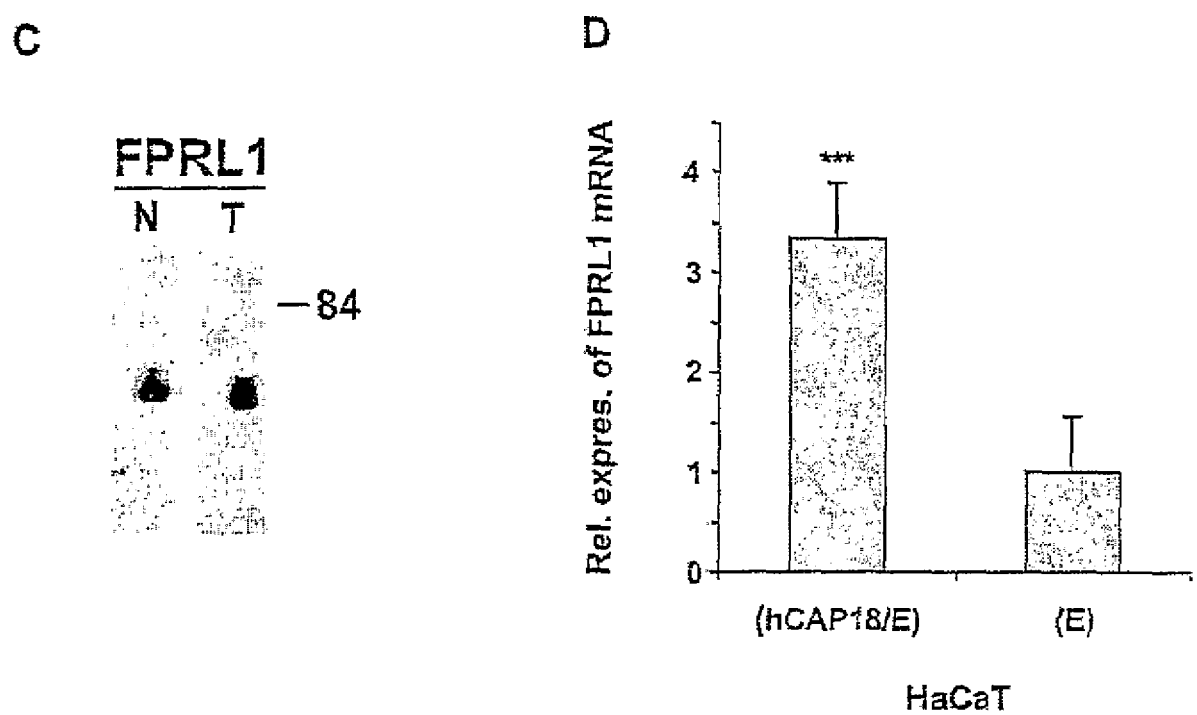

Figure 7:
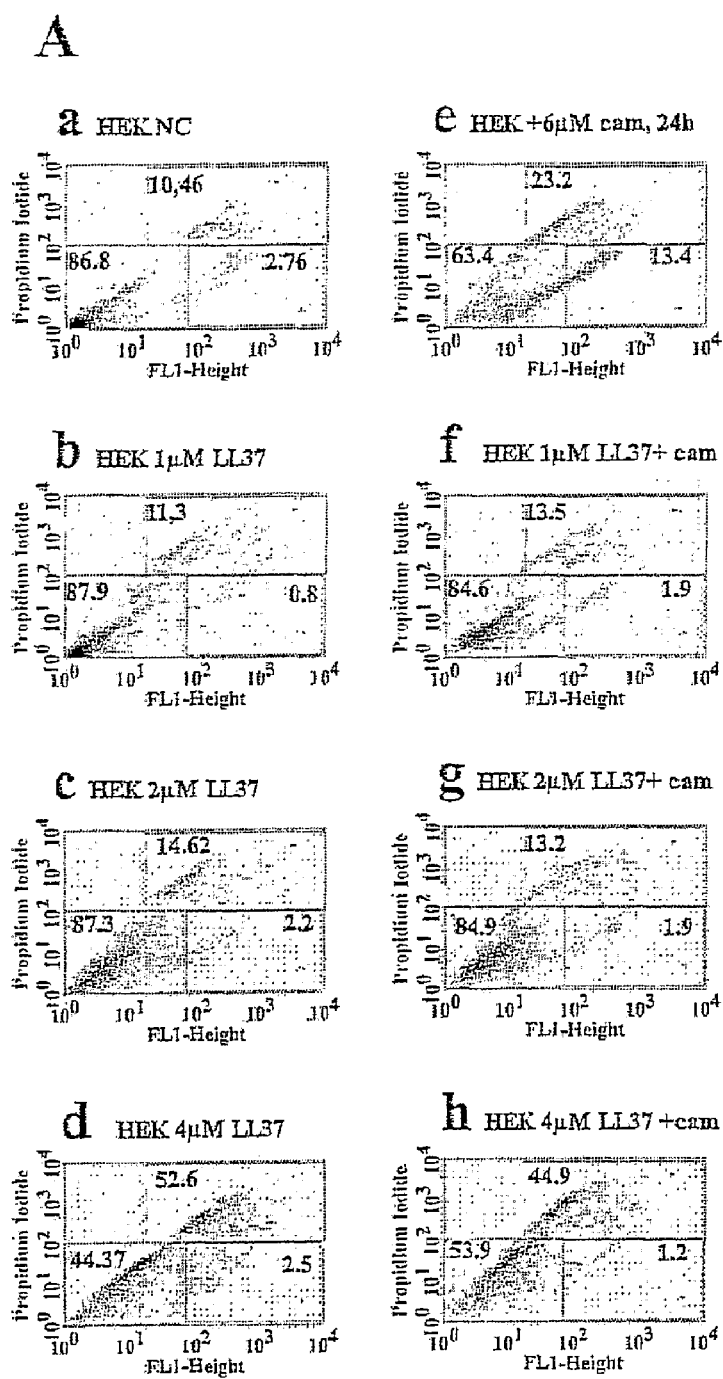

FIGURE 7 - *continued*
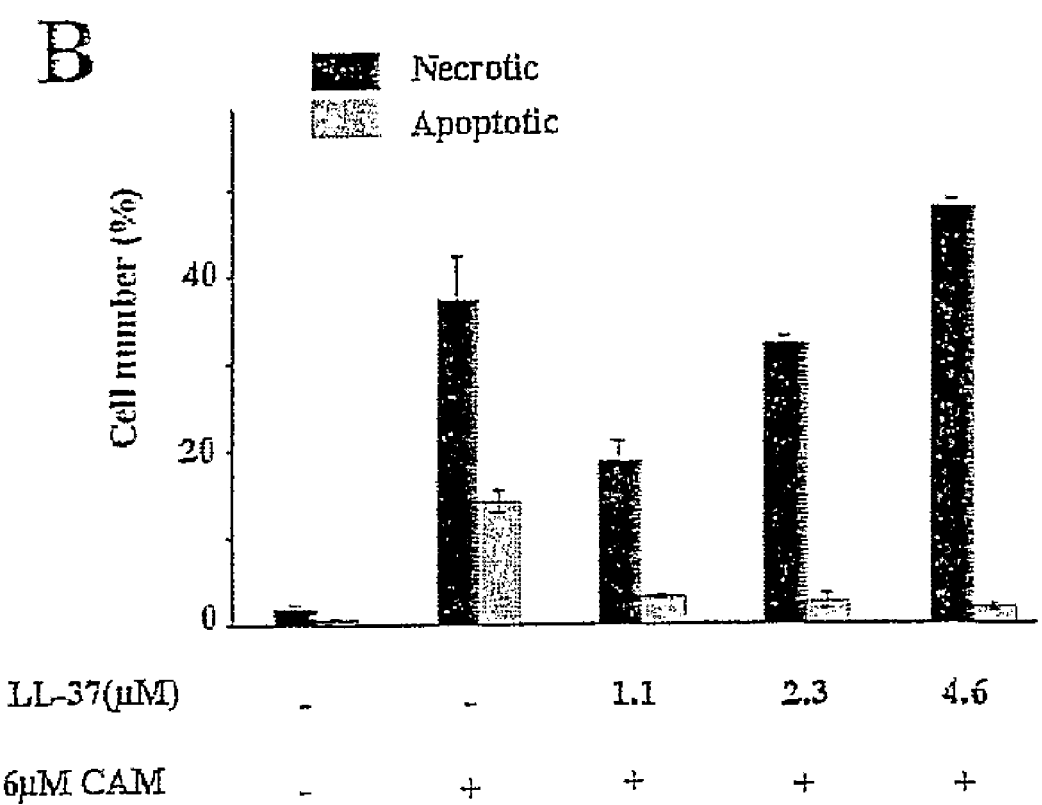

AGENTS AND USE THEREOF

This National Phase application claims priority under 35 U.S.C. 119(e) to U.S. Provisional Application No. 60/637,759 filed on Dec. 22, 2007. The entire content is hereby expressly incorporated by reference into the present application.

FIELD OF THE INVENTION

The present invention relates to agents for use in the treatment and diagnosis of cancer. In particular, the invention provides agents capable of inhibiting the proliferation of cancer cells.

INTRODUCTION

Antimicrobial proteins are key effectors in the innate immune system. Human cathelicidin antimicrobial protein hCAP18, the only known cathelicidin in humans, consists of a conserved cathelin domain and a variable C-terminus, called LL-37 (Gudmundsson et al., 1996, *Eur J Biochem* 1238:325-32; Zanetti et al., 1995, *FEBS Lett* 374:1-5). Extracellular proteolytic processing of the holoprotein releases the LL-37 peptide, which has broad antimicrobial activity (Gudmundsson et al., 1995, *Proc Natl Acad Sci USA* 92:7085-9; Agerberth et al., 1995, *Proc Natl Acad Sci USA* 92:195-99) as well as effects on host cells, some of which are mediated by the G-protein-coupled receptor, formyl peptide receptor-like 1 (FPRL1) (Yang et al., 2000, *J Exp Med* 192:1069-74; Koczulla et al., 2003, *J Clin Invest* 111:1665-72). hCAP18 is present in leucocytes (Cowland et al., 1995, *FEBS Lett* 368:173-76) and is expressed in sldn and other epithelia where it is upregulated in association with inflammation (Cowland et al., 1995, *FEBS Lett* 368:173-76; Frohm et al., 1997, *J Biol Chem* 272:15258-63) and injury (Dorschner et al., 2001, *J Invest Dermatol* 117:91-97; Heilborn et al., 2003, *J Invest Dermatol* 120:379-89) consistent with a role in innate barrier protection. Recently, antimicrobial proteins including cathelicidins have been proposed to also play a role in the non-specific host defence against tumours (Winder et al., 1998, *Biochem Biophys Res Commun* 242:608-12; Ohtake et al., 1999, *Br J Cancer* 181:393-403.).

SUMMARY OF INVENTION

A first aspect of the invention provides an agent for inhibiting the proliferation of cancer cells, wherein the agent inhibits (i.e. is capable of inhibiting in vivo) the biological activity of hCAP18/LL-37.

By an 'agent' we include all chemical entities, for example oligonucleotides, polynucleotide, polypeptides, peptidomimetics and small compounds.

Thus, the invention provides an agent capable of inhibiting the biological activity of hCAP18/LL-37 directly (for example, by reducing the biological activity of the protein) or indirectly (for example, by reducing expression of hCAP18/LL-37).

In a preferred embodiment, the agent inhibits the biological activity of hCAP18/LL-37 by altering the transcription, translation and/or binding properties of hCAP18/LL-37.

Such agents may be identified using methods well known in the art, such as:

(a) by determining the effect of a test agent on levels of expression of hCAP18/LL-37 mRNA, for example by Southern blotting or related hybridisation techniques;

(b) by determining the effect of a test agent on levels of hCAP18/LL-37 protein, for example by immunoassays using anti-hCAP18/LL-37 antibodies; and (c) by determining the effect of a test agent on a functional marker of hCAP18/LL-37 activity, for example phosphorylation of ErbB2.

In a preferred embodiment of the invention, the agent is an inhibitor of the transcription of hCAP18/LL-37.

In an alternative embodiment of the invention, the agent is an inhibitor of the translation of hCAP18/LL-37.

In a further embodiment of the invention, the agent is an inhibitor of the binding properties of hCAP18/LL-37. For example, the agent may alter the conformation of hCAP18/LL-37 such that it is no longer able to bind to its receptor.

It will be appreciated by persons skilled in the art that the agent may also inhibit the biological activity of hCAP18/LL-37 by blocking hCAP18/LL-37 receptor function directly, i.e. by acting as an hCAP18/LL-37 receptor antagonist. Preferably, the hCAP18/LL-37 receptor is FPRL1.

In a still further embodiment of the invention, the agent inhibits the biological activity of hCAP18/LL-37 by modulating (for example, reducing) the stability of hCAP18/LL-37 or its mRNA.

Advantageously, the agent is capable of inhibiting the biological activity of hCAP18/LL-37 selectively.

By 'selectively' we mean that the agent inhibits the biological activity of hCAP18/LL-37 to a greater extent than it modulates the activity of other proteins in the cancer cells. Preferably, the agent inhibits only the biological activity of hCAP18/LL-37, although it will be appreciated that the expression and activity of other proteins within the cancer cells may change as a downstream consequence of a selective inhibition of hCAP18/LL-37. Thus, we exclude agents which have a non-specific effect on gene expression and/or cancer cell growth.

It will be appreciated by persons skilled in the art that inhibition of the biological activity of hCAP18/LL-37 by an agent of the invention may be in whole or in part. For example, the agent may inhibit the biological activity of hCAP18/LL-37 by at least 10%, preferably at least 20%, 30%, 40%, 50%, 60%, 70%, 80% or 90%, and most preferably by 100% compared to the biological activity of hCAP18/LL-37 in cancer cells which have not been exposed to the agent. In a preferred embodiment, the agent is capable of inhibiting the biological activity of hCAP18/LL-37 by 50% or more compared to the biological activity of hCAP18/LL-37 in cancer cells which have not been exposed to the agent.

Preferably, the agent is selected from the following types of agent:
(a) short interfering RNA (siRNA) molecules;
(b) antisense oligonucleotides; and
(c) compounds, such as polypeptides, with binding affinity for hCAP18/LL-37.

Alternatively, the agent may be a small inhibitor compound such as antagonists to vitamin D, for example ZK159222 (Schering AG) and TEI-9647 (Tejin Institute for Medical Research, Tokyo), and antagonists to vitamin A, for example AGN193109 (Allergen Pharmaceuticals).

In a preferred embodiment of the first aspect of the invention, the agent is a short interfering RNA (siRNA) molecule.

RNA interference is a two-step process. The first step, which is termed as the initiation step, input dsRNA is digested into 21-23 nucleotide (nt) small interfering RNAs (siRNA), probably by the action of Dicer, a member of the Rnase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA) each with 2-nucleotide 3' overhangs (Hutvagner & Zamore, 2002, *Curr. Opin. Genetics and Development* 12:225-232; Bernstein, 2001, *Nature* 409:363-366).

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA (Hutvagner & Zamore, 2002, supra.; Hammond et al., 2001, *Nat. Rev. Gen.* 2:110-119 (2001); Sharp, 2001, *Genes. Dev.* 15:485-90). Although the mechanism of cleavage is still to be elucidated, research indicates that each RISC contains a single siRNA and an RNase (Hutvagner & Zamore, 2002, supra.).

In view of the remarkable potency of RNAi, an amplification step within the RNAi pathway has been suggested. Amplification could occur by copying of the input dsRNAs which would generate more siRNAs, or by replication of the siRNAs formed. Alternatively, or additionally, amplification could be effected by multiple turnover events of the RISC (Hammond et al., 2001, supra.; Hutvagner & Zamore, 2002, supra.). Additional information on RNAi can be found in the following reviews, Tuschl, 2001, *Chem. Biochem.* 2:239-245, Cullen, 2002, *Nat. Immunol.* 3:597-599 and Brantl, 2002, *Biochem. Biophys Act.* 1575:15-25.

Synthesis of RNAi molecules suitable for use with the present invention can be effected as follows. First, the hCAP18/LL-37 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex (Tuschl, *Chem Biochem.* 2:239-245). It will be appreciated, however, that siRNAs directed at untranslated regions may also be effective.

Second, potential target sites are compared to an appropriate genomic database (e.g. human, mouse, rat, etc.) using sequence alignment software, such as the BLAST (see NCBI website). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Preferably, the siRNA molecule comprises a fragment of the nucleotide sequence of SEQ ID NO:1, or a variant of such a fragment.

```
HCAP18/LL-37 mRATA (Accession No. MN 004345)
                                                            [SEQ ID NO: 1]
  1 taaagcaaac cccagcccac accctggcag gcagccaggg atgggtggat caggaaggct 61 cctggttggg cttttgcatc aggctcaggc tgggcataaa ggaggctcct gtgggctaga 121 gggaggcaga catgggggacc atgaagaccc aaagggatgg ccactccctg gggcggtggt 181 cactggtgct cctgctgctg ggcctggtga tgcctctggc catcattgcc caggtcctca 241 gctacaagga agctgtgctt cgtgctatag atggcatcaa ccagcggtcc tcggatgcta 301 acctctaccg cctcctggac ctggacccca ggcccacgat ggatggggac ccagacacgc 361 caaagcctgt gagcttcaca gtgaaggaga cagtgtgccc caggacgaca cagcagtcac 421 cagaggattg tgacttcaag aaggacgggc tggtgaagcg gtgtatgggg acagtgaccc 481 tcaaccaggc caggggctcc tttgacatca gttgtgataa ggataacaag agatttgccc 541 tgctgggtga tttcttccgg aaatctaaag agaagattgg caaagagttt aaaagaattg 601 tccagagaat caaggatttt ttgcggaatc ttgtacccag gacagagtcc tagtgtgtgc 661 cctaccctgg ctcaggcttc tgggctctga gaaataaact atgagagcaa tttcaaaaaa 721 aaaaaaaaaa aaaaaaaaa
```

Alternatively, the siRNA molecule comprises a fragment of the nucleotide sequence derived from ENSG00000164047 (genomic sequence).

By "fragment" we mean at least 10 nucleotides, for example at least 15, 16, 17, 18, 19, 20, 21, 22, 23, 24 or 25 nucleotides.

By "variant" we mean that the nucleotide sequence shares at least 90% sequence identity with a fragment of SEQ ID NO:1, for example at least 95%, 96%, 97%, 98% or 99% sequence identity.

The percent sequence identity between two polynucleotides may be determined using suitable computer programs, for example the GAP program of the University of Wisconsin Genetic Computing Group and it will be appreciated that percent identity is calculated in relation to polynucleotides whose sequences have been aligned optimally.

The alignment may alternatively be carried out using the Clustal W program (as described in Thompson et al., 1994, *Nuc. Acid Res.* 22:4673-4680).

The parameters used may be as follows:

Fast pairwise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

Advantageously, the siRNA molecule is 19 to 23 nucleotides in length.

In an alternative preferred embodiment of the first aspect of the invention, the agent is an antisense oligonucleotide.

The design of antisense molecules which can be used to decrease efficiently hCAP18/LL-37 levels/activity requires consideration of two aspects important to the antisense approach. The first aspect is delivery of the oligonucleotide into the cytoplasm of the cancer cells, while the second aspect is design of an oligonucleotide which specifically binds the designated mRNA within cells in a way which inhibits translation thereof.

The prior art teaches a number of delivery strategies which can be used to efficiently deliver oligonucleotides into a wide variety of cell types (for example, see Luft, 1998, *J Mol Med* 76:75-6; Kronenwett et al., 1998, *Blood* 91:852-62; Rajur et al., 1997, *Bioconjug Chem* 8:935-40; Lavigne et al., 1997, *Biochem Biophys Res Commun* 237:566-71; Aoki et al., 1997, *Biochem Biophys Res Commun* 231:540-5).

In addition, algorithms for identifying those sequences with the highest predicted binding affinity for their target mRNA based on a thermodynamic cycle that accounts for the energetics of structural alternations in both the target mRNA and the oligonucleotide are available (for example, see Walton et al., 1999, *Biotechnol Bioeng* 65:1-9).

Several approaches for designing and predicting efficiency of specific oligonucleotides using an in vitro system are also known (for example, see Matveeva et al., 1998, *Nature biotechnology* 16:1374-1375).

Several clinical trails have demonstrated safety, feasibility and activity of antisense oligonucleotides. For example, antisense oligonucleotides suitable for the treatment of cancer have been successfully used (Hohmlund et al., 1999, *Curr Opin Mol Ther* 1:372-85; Gerwitz, 1999, *Curr Opin Mol Ther* 1:297-306). More recently, antisense-mediated suppression of human heparanase gene expression has been reported to inhibit pleural dissemination of human cancer cells in a mouse model (Uno et al., 2001, *Cancer Res* 61:7855-60).

Thus, persons skilled in the art are readily able to design and implement antisense approaches suitable for downregulating expression of hCAP18/LL-37.

Preferably, the antisense oligonucleotide comprises a fragment of the nucleotide of SEQ ID NO:1, or a variant of such a fragment.

Advantageously, the antisense oligonucleotide is 15 to 35 bases in length. For example, 20-mer oligonucleotides have been shown to inhibit the expression of the epidermal growth factor receptor mRNA (Witters et al, *Breast Cancer Res Treat* 53:41-50 (1999)) and 25-mer oligonucleotides have been shown to decrease the expression of adrenocorticotropic hormone by greater than 90% (Franlel et al, *J Neurosurg* 91:261-7 (1999)). However, it is appreciated that it may be desirable to use oligonucleotides with lengths outside this range, for example 10, 11, 12, 13, or 14 bases, or 36, 37, 38, 39 or 40 bases.

It will be further appreciated by person skilled in the art that oligonucleotides are subject to being degraded or inactivated by cellular endogenous nucleases. To counter this problem, it is possible to use modified oligonucleotides, e.g. having altered internucleotide linkages, in which the naturally occurring phosphodiester linkages have been replaced with another linkage. For example, Agrawal et al (1988) *Proc. Natl. Acad. Sci. USA* 85, 7079-7083 showed increased inhibition in tissue culture of HIV-1 using oligonucleotide phosphoramidates and phosphorotinoates. Sarin et al (1988) *Proc. Natl. Acad. Sci. USA* 85, 7448-7451 demonstrated increased inhibition of HIV-1 using oligonucleotide methylphosphonates. Agrawal et al (1989) *Proc. Natl. Acad. Sci. USA* 86, 7790-7794 showed inhibition of HIV-1 replication in both early-infected and chronically infected cell cultures, using nucleotide sequence-specific oligonucleotide phosphorothioates. Leither et al (1990) *Proc. Natl. Acad. Sci USA* 87, 3430-3434 report inhibition in tissue culture of influenza virus replication by oligonucleotide phosphorothioates.

Oligonucleotides having artificial linkages have been shown to be resistant to degradation in vivo. For example, Shaw et al (1991) in *Nucleic Acids Res.* 19, 747-750, report that otherwise unmodified oligonucleotides become more resistant to nucleases in vivo when they are blocked at the 3' end by certain capping structures and that uncapped oligonucleotide phosphorothioates are not degraded in vivo.

A detailed description of the H-phosphonate approach to synthesising oligonucleoside phosphorothioates is provided in Agrawal and Tang (1990) *Tetrahedron Letters* 31, 7541-7544, the teachings of which are hereby incorporated herein by reference. Syntheses of oligonucleoside methylphosphonates, phosphorodithioates, phosphoramidates, phosphate esters, bridged phosphorarnidates and bridge phosphorothioates are known in the art. See, for example, Agrawal and Goodchild (1987) *Tetrahedron Letters* 28, 3539; Nielsen et al (1988) *Tetrahedron Letters* 29, 2911; Jager et al (1988) *Biochemnistiy* 27, 7237; Uznanski et al (1987) *Tetrahedron Letters* 28, 3401; Bannwarth (1988) *Helv. Chim. Acta.* 71, 1517; Crosstick and Vyle (1989) *Tetrahedron Letters* 30, 4693; Agrawal et al (1990) *Proc. Natl. Acad. Sci. USA* 87, 1401-1405, the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesised and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridisation and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial intemucleotide linkages for the native phosphodiester linkages, for example, by replacing phosphate with sulphur in the linkage. Examples of linkages that may be used include phosphorothioates, methylphosphonates, sulphone, sulphate, ketyl, phosphorodithioates, various phosphoramidates, phosphate esters, bridged phosphorothioates and bridged phosphoramidates. Such examples are illustrative, rather than limiting, since other intemucleotide linkages are well known in the art. The synthesis of oligonucleotides having one or more of these linkages substituted for the phosphodiester intemucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-Link II™ from Applied BioSystems Inc, Foster City, Calif. Methods for capping are described, for example, by Shaw et al (1991) *Nucleic Acids Res.* 19, 747-750 and Agrawal et al (1991) *Proc. Natl. Acad. Sci. USA* 88(17), 7595-7599.

A further method of making oligonucleotides resistant to nuclease attack is for them to be "self-stabilised" as described by Tang et al (1993) *Nucl. Acids Res.* 21, 2729-2735. Self-stabilised oligonucleotides have hairpin loop structures at their 3' ends, and show increased resistance to degradation by snake venom phosphodiesterase, DNA polymerase I and foetal bovine serum. The self-stabilised region of the oligonucleotide does not interfere in hybridisation with complementary nucleic acids, and pharnacokinetic and stability studies in mice have shown increased in vivo persistence of self-stabilised oligonucleotides with respect to their linear counterparts.

In a further preferred embodiment of the agents of the invention, the agent is a compound with binding affinity for hCAP18/LL-37, such as proteins and carbohydrates.

By "a compound with binding affinity" we mean a compound which is capable of binding to hCAP18/LL-37 in vivo, i.e. under the physiological conditions in which hCAP18/LL-37 exists inside cancer cells.

For example, the compound may bind substantially reversibly or substantially irreversibly to an active site of hCAP18/LL-37. In a further example, the compound may bind to a portion of hCAP18/LL-37 that is not the active site so as to interfere with the binding of the hCAP18/LL-37 to a ligand or receptor. In a still further example, the compound may bind to a portion of hCAP18/LL-37 so as to decrease the proteins activity by an allosteric effect. This allosteric effect may be an allosteric effect that is involved in the natural regulation of the activity of hCAP18/LL-37, for example in the activation of the hCAP18/LL-37 by an "upstream activator".

Methods for detecting interactions between a test compound and hCAP18/LL-37 are well known in the art. For example ultrafiltration with ion spray mass spectroscopy/HPLC methods or other physical and analytical methods may be used. In addition, Fluorescence Energy Resonance Transfer (FRET) methods may be used, in which binding of two fluorescent labelled entities may be measured by measuring the interaction of the fluorescent labels when in close proximity to each other.

Alternative methods of detecting binding of a polypeptide to macromolecules, for example DNA, RNA, proteins and phospholipids, include a surface plasmon resonance assay, for example as described in Plant et al., 1995, *Analyt Biochem* 226(2), 342-348. Methods may make use of a polypeptide that is labelled, for example with a radioactive or fluorescent label.

A further method of identifying a compound that is capable of binding to the polypeptide is one where the polypeptide is exposed to the compound and any binding of the compound to the said polypeptide is detected and/or measured. The binding constant for the binding of the compound to the polypeptide may be determined. Suitable methods for detecting and/or measuring (quantifying) the binding of a compound to a polypeptide are well known to those skilled in the art and may be performed, for example, using a method capable of high throughput operation, for example a chip-based method. New technology, called VLSIPS™, has enabled the production of extremely small chips that contain hundreds of thousands or more of different molecular probes. These biological chips or arrays have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Another method of identifying compounds with binding affinity for hCAP18/LL-37 is the yeast two-hybrid system, where the polypeptides of the invention can be used to "capture" proteins that bind hCAP18/LL-37. The yeast two-hybrid system is described in Fields & Song, *Nature* 340:245-246 (1989).

In a preferred embodiment of this aspect of the invention, the agent is a compound which has ligand-binding capacity for hCAP18/LL-37.

For example, the agent may be a soluble fragment of an hCAP18/LL-37 receptor (such as FPRL1). Alternatively, the agent may be a high affinity molecule that mimics an antibody (a so-called 'affibody') (for example, see U.S. Pat. No. 5,831, 012 and the affibody website). These ligands are small, simple proteins composed of a three-helix bundle based on the scaffold of one of the IgG-binding domains of Protein A (a surface protein from the bacterium *Staphylococcus aureus*). This scaffold has excellent features as an affinity ligand and can be designed to bind with high affinity to any given target protein.

Advantageously, however, the compound with binding affinity for hCAP18/LL-37 is or comprises a polypeptide.

For example, the compound may be an antibody, such as a monoclonal or polyclonal antibody, or an antigen-binding fragment thereof.

By "antibody" we include substantially intact antibody molecules, as well as chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to hCAP18/LL-37.

Preferably, the antigen-binding fragment is selected from the group consisting of Fv fragments (e.g single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]).

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

Also included within the scope of the invention are modified versions of antibodies and an antigen-binding fragments thereof, e.g. modified by the covalent attachment of polyethylene glycol or other suitable polymer.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Antibody fragments can be obtained using methods well known in the art (see, for example, Harlow & Lane, 1988, "*Antibodies: A Laboratory Manual*", Cold Spring Harbor Laboratory, New York). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Riechmann et al., 1988. *Nature* 332:323-327; Verhoeyen et al., 1988, *Science* 239: 1534-15361; U.S. Pat. No. 4,816,567) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95).

Once suitable antibodies are obtained, they may be tested for activity, for example by ELISA.

In a particularly preferred embodiment of the first aspect of the invention, the agent is capable of being selectively delivered to or selectively activated by the cancer cells.

By "selectively" we mean that the inhibitory action of the agent on the biological activity of hCAP18/LL-37 is preferentially exerted at or within the cancer cells (other than by local administration of the agent to the site of cancer cells).

Methods for targeting agents to particular cell types, such as cancer cells, are well known in the art (for example see Vasir & Labhasetwar, 2005, *Technol Cancer Res Treat.* 4(4): 363-74; Brannon-Peppas & Blanchette, 2004, *Adv Drug Deliv Rev.* 56(11):1649-59 and Zhao & Lee, 2004, *Adv Drug Deliv Rev.* 56(8):1193-204).

For example, the agent may comprise a target cell specific portion.

By "target cell specific" portion we mean the portion of the agent which comprises one or more binding sites which recognise and bind to entities on the target cancer cell. Upon contact with the target cell, the target cell specific portion may be internalised along with the inhibitor portion.

The entities recognised by the target cell-specific portion are expressed predominantly, and preferably exclusively, on the target cancer cell. The target cell specific portion may contain one or more binding sites for different entities expressed on the same target cell type, or one or more binding sites for different entities expressed on two or more different target cell types.

Preferably, the target cell-specific portion recognises the target cell with high avidity.

By "high avidity" we mean that the target cell-specific portion recognises the target cell with a binding constant of at least $K_d=10^{-6}$ M, preferably at least $K_d=10^{-9}$ M, suitably $K_d=10^{-10}$ M, more suitably $K_d=10^{-11}$ M, yet more suitably still $K_d=10^{-12}$ M, and more preferably $K_d=10^{-15}$ M or even $K_d=10^{-18}$ M.

The entity which is recognised may be any suitable entity which is expressed by tumour cells. Often, the entity which is recognised will be an antigen.

Examples of antigens include those listed in Table 1.

TABLE 1

| Tumour Associated Antigens | | |
|---|---|---|
| Antigen | Antibody | Existing Uses |
| Carcino-embryonic Antigen | C46 (Amersham) 85A12 (Unipath) | Imaging & Therapy of colon/rectum tumours. |
| Placental Alkaline Phosphatase | H17E2 (ICRF, Travers & Bodmer) | Imaging & Therapy of testicular and ovarian cancers. |

TABLE 1-continued

Tumour Associated Antigens

| Antigen | Antibody | Existing Uses |
| --- | --- | --- |
| Pan Carcinoma | NR-LU-10 (NeoRx Corporation) | Imaging & Therapy of various carcinomas incl. small cell lung cancer. |
| Polymorphic Epithelial Mucin (Human milk fat globule | HMFG1 (Taylor-Papadimitriou, ICRF) (Antisoma plc) | Imaging & Therapy of ovarian cancer, pleural effusions, breast, lung & other common epithelial cancers. |
| Human milk mucin core protein | SM-3(IgG1)[1] | Diagnosis, Imaging & Therapy of breast cancer |
| β-human Chorionic Gonadotropin | W14 | Targeting of enzyme (CPG2) to human xenograft choriocarcinoma in nude mice. (Searle et al (1981) Br. J. Cancer 44, 137-144) |
| A Carbohydrate on Human Carcinomas | L6 (IgG2a)[2] | Targeting of alkaline phosphatase. (Senter et al (1988) Proc. Natl. Acad. Sci. USA 85, 4842-4846 |
| CD20 Antigen on B Lymphoma (normal and neoplastic) | 1F5 (IgG2a)[3] | Targeting of alkaline phosphatase. (Senter et al (1988) Proc. Natl. Acad. Sci. USA 85, 4842-4846 |

[1] Burchell et al (1987) Cancer Res. 47, 5476-5482
[2] Hellström et al (1986) Cancer Res. 46, 3917-3923
[3] Clarke et al (1985) Proc. Natl. Acad. Sci. USA 82, 1766-1770

Other antigens include alphafoetoprotein, Ca-125, prostate specific antigen and members of the epidermal growth factor receptor family, namely EGFR, erb B3 and erb B4.

Advantageously, the target cell specific portion is an antibody (e.g. a monoclonal antibody) or antigen-binding fragment thereof. Preferably, the antibody is a humanised antibody.

Conveniently, the target cell-specific portion comprises two or more binding sites for the target cell, wherein the target cell specific portion is an antibody, or bivalent fragment thereof. Said target cell specific portion may have respective 'arms' that recognise the same entity as one another or that recognise different entities.

In one embodiment of the agents of the invention, the target cell specific portion has two 'arms' which recognise different molecules on the same target cell wherein the molecules on the same target cell are not confined to that cell type but may occur on a few other cell types. For example, one 'arm' of the target cell-specific portion may recognise molecules on cell types I, II and III, whereas the other 'arm' may recognise molecules on cell types I, IV and V. Thus, an agent of the invention comprising such a target cell-specific portion will have greater specificity for cell type I compared with cell types II, III and IV. This aspect of the invention is particularly helpful, as there have been very few completely target cell-specific molecules discovered, whereas molecules which occur on a few cell types, and which are useful in this aspect of the invention, are well known. Such molecules are usually cell-surface antigens for which cross-reactive antibodies are known.

Monoclonal antibodies which will bind to many of the antigens listed in Table 1 are already known, but in any case, with today's techniques in relation to monoclonal antibody technology, antibodies can be prepared to most antigens (see above).

The entity that is recognised may or may not be antigenic but can be recognised and selectively bound to in some other way. For example, it may be a characteristic cell surface receptor such as the receptor for melanocyte-stimulating hormone (MSH) which is expressed in high number in melanoma cells. Alternatively, the entity may be an entity that is induced in the target cells. The cell-specific portion may then be a compound or part thereof which specifically binds to the entity in a non-imnmune sense, for example as a substrate or analogue thereof for a cell-surface enzyme or as a messenger.

Preferably, the high avidity target cell specific portion comprises two or more different binding sites for the target cell.

The different binding sites for the target cell may or may not be two or more different antibodies, or fragments thereof, which are directed to different entities expressed on the target cell. Alternatively, the different binding sites for the target cell may recognise and selectively bind the cell in some other, non-immune sense.

It will be appreciated that the targeting portion may be joined to the inhibitor agent of the invention by any suitable means which retains the functional activity of two portions. For example, where the targeting portion and the inhibitor portion are both polypeptides, they may be fused to each other to create a fusion polypeptide. Examples of such fusions are well known to those skilled in the art.

In an alternative embodiment of the selective inhibitory agents on the invention, the agent is a prodrug selectively activated by the cancer cell.

The term "prodrug" as used in this application refers to a precursor or derivative form of a pharmaceutically active substance that is less cytotoxic to cancer cells compared to the parent drug and is capable of being enzymatically activated or converted into the more active parent form (see, for example, D. E. V. Wilman "Prodrugs in Cancer Chemotherapy" *Biochemical Society Triansactions* 14, 375-382 (615th Meeting, Belfast 1986) and V. J. Stella et al "Prodrugs: A Chemical Approach to Targeted Drug Delivery" *Directed Drug Delivery* R. Borchardt et al (ed.) pages 247-267 (Humana Press 1985)).

Suitable methods for producing such prodrug agents are well known in the art (for example, see Denny, 2004, *Cancer Invest.* 22(4):604-19; Rooseboom et al., 2004, *Pharmacol Rev.* 2004 56(1):53-102; WO 03/106491).

Several factors need to be taken into account in selecting an enzyme for prodrug activation. These include the molecular weight and physical properties of the enzyme, its activity and stability under physiological conditions, and the nature of the drug that the enzyme generates.

The adaptability of the strategy caters for the employment of a variety of enzymes which have the potential to release a multitude of mechanistically separate anticancer agents. Of particular value is the fact that a single Mab-enzyme conjugate can generate therapeutically effective doses of mechanistically distinct anticancer agents possessing synergistic activities. This should prove important for immunogenicity reasons. In these respects, many β-lactamases hold a great deal of potential because of their favourable kinetics and broad substrate specificities, as well as their abilities to effect the elimination of substituents appended to the 3'-position of cephalosporin substrates (see Svensson et al (1992) "Mab-β-lactamase conjugates for the activation of a cephalosporin mustard prodrug" *Bioconjugate Chem.* 3, 176-181).

Enzymes of both mammalian and non-mammalian origin have been used for the activation of a wide range of prodrugs (Senter et al, 1993. Generation of cytotoxic agents by targeted enzymes. Bioconjugate 4, 3-9; Senter ef al, 1991. Activation of prodrugs by antibody-enzyme conjugates. In Immunobiology of Proteins and Peptides VI, ed. M. Z. Atassi. Plenum Press, New York, pp 97-105). While enzymes of mammalian origin might be advantageous due to reduced immunogenicity, the prodrugs that they act upon might be substrates for corresponding endogenous enzymes.

It will be appreciated by persons skilled in the art that the agents of the invention may be used to inhibit the proliferation of different types of cancer cell. In a preferred embodiment, however, the cancer cells (carcinoma cells) are epithelial cells or squamous cells.

Advantageously, the cancer cells are selected from the group consisting of cancer cells of the breast, bile duct, brain, colon, stomach, reproductive organs, lung and airways, skin, gallbladder, liver, nasopharynx, nerve cells, kidney, prostate, lymph glands and gastrointestinal tract.

Preferably, the cancer cells are breast cancer cells. More preferably, the breast cancer cells are Elston grade III cells. Most preferably, the breast cancer cells are metastatic.

A second aspect of the invention provides a pharmaceutical composition comprising an agent according to the first aspect of the invention and a pharmaceutically acceptable excipient, diluent or carrier. Thus, the invention further provides medicaments for inhibiting the proliferation of cancer cells.

As used herein, 'pharmaceutical formulation' means a therapeutically effective formulation according to the invention.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

Thus, in a preferred embodiment, the present invention provides a pharmaceutical formulation comprising an amount of an agent of the invention sufficient to inhibit the activity of hCAP18/LL-37 in cancer cells and a pharmaceutically acceptable carrier.

It will be appreciated by persons skilled in the art that such an effective amount of the agent or formulation thereof may be delivered as a single bolus dose (i.e. acute administration) or, more preferably, as a series of doses over time (i.e. chronic administration).

The agents of the invention can be formulated at various concentrations, depending on the efficacy/toxicity of the compound being used and the indication for which it is being used. Preferably, the formulation comprises the agent of the invention at a concentration of between 0.1 µM and 1 mM, more preferably between 1 µM and 100 µM, between 5 µM and 50 µM, between 10 µM and 50 µM, between 20 µM and 40 µM and most preferably about 30 µM. For in vitro applications, formulations may comprise a lower concentration of a compound of the invention, for example between 0.0025 µM and 1 µM.

It will be appreciated by persons skilled in the art that the agents of the invention will generally be administered in admixture with a suitable pharmaceutical excipient diluent or carrier selected with regard to the intended route of administration and standard pharmaceutical practice (for example, see Remington: The Science and Practice of Pharmacy, $19^{th}$ edition, 1995, Ed. Alfonso Gennaro, Mack Publishing Company, Pennsylvania, USA).

For example, the agents of the invention can be administered orally, buccally or sublingually in the form of tablets, capsules, ovules, elixirs, solutions or suspensions, which may contain flavouring or colouring agents, for immediate-, delayed- or controlled-release applications. The agents of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The agents of the invention can also be administered parenterally, for example, intravenously, intra-articularly, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the agents of the invention will usually be from 1 to 1000 mg per adult (i.e. from about 0.015 to 15 mg/kg), administered in single or divided doses.

The agents of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the agents of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For ophthalmic use, the agents of the invention can be formulated as micronised suspensions in isotonic, pH adjusted, sterile saline, or, preferably, as solutions in isotonic, pH adjusted, sterile saline, optionally in combination with a preservative such as a benzylaliconium chloride. Alternatively, they may be formulated in an ointment such as petrolatum.

For application topically to the skin, the agents of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or creamn, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Where the agent is a polypeptide, it may be preferable to use a sustained-release drug delivery system, such as a microspheres. These are designed specifically to reduce the frequency of injections. An example of such a system is Nutropin Depot which encapsulates recombinant human growth hormone (rhGH) in biodegradable microspheres that, once injected, release rhGH slowly over a sustained period.

Alternatively, polypeptide agents of the present invention can be administered by a surgically implanted device that releases the drug directly to the required site.

Electroporation therapy (EPT) systems can also be employed for the administration of proteins and polypeptides. A device which delivers a pulsed electric field to cells increases the permeability of the cell membranes to the drug, resulting in a significant enhancement of intracellular drug delivery.

Proteins and polypeptides can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of protein and polypeptide delivery is the thermo-sensitive ReGel injectable. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Protein and polypeptide pharmaceuticals can also be delivered orally. One such system employs a natural process for oral uptake of vitamin B12 in the body to co-deliver proteins and polypeptides. By riding the vitamin B12 uptake system, the protein or polypeptide can move through the intestinal wall. Complexes are produced between vitamin B12 analogues and the drug that retain both significant affinity for intrinsic factor (IF) in the vitamin B12 portion of the complex and significant bioactivity of the drug portion of the complex.

Methods for administering oligonucleotide or polynucleotide agents of the invention are also well know in the art (see Dass, 2002, *J Pharm Pharmacol.* 54(1):3-27; Dass, 2001, *Drug Deliv.* 8(4):191-213; Lebedeva et al., 2000, *Eur J Pharm Biopharm.* 50(1):101-19; Pierce et al., 2005, *Mini Rev, Med Chem.* 5(1):41-55; Lysik & Wu-Pong, 2003, *J Pharm Sci.* 2003 2(8):1559-73; Dass, 2004, *Biotechnol Appl Biochem.* 40(Pt 2):113-22; Medina, 2004, *Curr Pharm Des.* 10(24):2981-9.

For example, the constructs of the invention may be introduced into cells by methods involving retroviruses, so that the construct is inserted into the genome of the cell. For example, in Kuriyama et al (1991) *Cell Struc. and Func.* 16, 503-510 purified retroviruses are administered. Retroviral DNA constructs comprising a polynucleotide as described above may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a neo$^R$ gene). Independent colonies are isolated and expanded and the culture supernatant removed, filtered through a 0.45 µm pore-size filter and stored at −70° C. For the introduction of the retrovirus into the tumour cells, it is convenient to inject directly retroviral supernatant to which 10 μg/ml Polybrene has been added. For tumours exceeding 10 mm in diameter it is appropriate to inject between 0.1 ml and 1 ml of retroviral supernatant; preferably 0.5 ml.

Alternatively, as described in Culver et al (1992) *Science* 256, 1550-1552, cells which produce retroviruses are injected. The retrovirus-producing cells so introduced are engineered to actively produce retroviral vector particles so that continuous productions of the vector occurred within the tumour mass in situ. Thus, proliferating cells can be successfully transduced in vivo if mixed with retroviral vector-producing cells.

Targeted retroviruses are also available for use in the invention; for example, sequences conferring specific binding affinities may be engineered into pre-existing viral env, genes (see Miller & Vile (1995) *Faseb J.* 9, 190-199 for a review of this and other targeted vectors for gene therapy).

Other methods involve simple delivery of the construct into the cell for expression therein either for a limited time or, following integration into the genome, for a longer time. An example of the latter approach includes liposomes (Nassander et al (1992) *Cancer Res.* 52, 646-653).

For the preparation of immuno-liposomes MPB-PE (N-[4-(p-maleimidophenyl)butyryl]-phosphatidylethanolamine) is synthesised according to the method of Martin & Papahadjopoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with the agent of the invention (such as DNA or other genetic construct) for delivery to the target cells, for example, by forming the said liposomes in a solution of the agent, followed by sequential extrusion through polycarbonate membrane filters with 0.6 μm and 0.2 μm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected intraperitoneally or directly into the tumour.

Other methods of delivery include adenoviruses carrying external DNA via an antibody-polylysine bridge (see Curiel *Prog. Med. Virol.* 40, 1-18) and transferrin-polycation conjugates as carriers (Wagner et al (1990) *Proc. Natl. Acad. Sci. USA* 87, 3410-3414). In the first of these methods a polycation-antibody complex is formed with an oligonucleotide agent of the invention, wherein the antibody is specific for either wild-type adenovirus or a variant adenovirus in which a new epitope has been introduced which binds the antibody.

The polycation moiety binds the oligonucleotide agent via electrostatic interactions with the phosphate backbone. The adenovirus, because it contains unaltered fibre and penton proteins, is internalised into the cell and carries into the cell with it the oligonucleotide agent of the invention. It is preferred if the polycation is polylysine.

The oligonucleotide agent may also be delivered by adenovirus wherein it is present within the adenovirus particle, for example, as described below.

In an alternative method, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulfide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the tumour cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) *Proc. Natl. Acad. Sci. USA* 89, 6094-6098 may also be used. This approach appears to rely on the fact that adenoviruses are adapted to allow release of their DNA from an endosome without passage tnrough the lysosome, and in the presence of, for example transferrin linked to the DNA construct or other genetic construct of the invention, the construct is taken up by the cell by the same route as the adenovirus particle.

This approach has the advantages that there is no need to use complex retroviral constructs; there is no permanent modification of the genome as occurs with retroviral infection; and the targeted expression system is coupled with a targeted delivery system, thus reducing toxicity to other cell types.

It will be appreciated that "naked DNA" and DNA complexed with cationic and neutral lipids may also be useful in introducing the DNA of the invention into cells of the individual to be treated. Non-viral approaches to gene therapy are described in Ledley (1995) *Human Gene Therapy* 6, 1129-1144.

Alternative targeted delivery systems are also known such as the modified adenovirus system described in WO 94/10323 wherein, typically, the DNA is carried within the adenovirus, or adenovirus-like, particle. Michael et al (1995) *Gene Therapy* 2, 660-668 describes modification of adenovirus to add a cell-selective moiety into a fibre protein. Mutant adenoviruses which replicate selectively in p53-deficient human tumour cells, such as those described in Bischoff et at (1996) *Science* 274, 373-376 are also useful for delivering the genetic construct of the invention to a cell. Thus, it will be appreciated that a further aspect of the invention provides a virus or virus-like particle comprising a genetic construct of the invention. Other suitable viruses or virus-like particles include HSV, AAV, vaccinia and parvovirus.

In a further embodiment the agent which selectively prevents the function of hCAP18/LL-37 is a ribozyme capable of cleaving targeted hCAP18/LL-37 mRNA or DNA. A gene expressing said ribozyme may be administered in substantially the same and using substantially the same vehicles as for antisense molecules.

Ribozymes which may be encoded in the genomes of the viruses or virus-like particles herein disclosed are described in U.S. Pat. No. 5,180,818, U.S. Pat. No. 5,168,053, U.S. Pat. No. 5,149,796, U.S. Pat. No. 5,116,742, U.S. Pat. No. 5,093,246 and U.S. Pat. No. 4,987,071.

It will be appreciated that it may be desirable that the antisense molecule or ribozyme is expressed from a cell-specific promoter element.

In a particularly preferred embodiment of the formulations of the invention, the formulation is capable of targeted delivery of the agents of the invention to cancer cells.

Persons skilled in the art will further appreciate that the agents and pharmaceutical formulations of the present invention have utility in both the medical and veterinary fields. Thus, the agents of the invention may be used in the treatment of both human and non-human animals (such as horses, dogs and cats). Preferably, however, the patient is human.

A third aspect of the invention provides a method for inhibiting the proliferation of cancer cells in a patient, the method comprising administering to the patient a agent according to the first aspect of the invention or a pharmaceutical formulation according to the second aspect of the invention.

Preferably, the patient is human.

Advantageously, the agent is selectively delivered to or selectively activated by the cancer cells.

Thus, the invention further provides an agent according to the first aspect of the invention for use in medicine.

Preferably, the agent is for use in the treatment of cancer.

By 'treatment' we include both therapeutic and prophylactic treatment of the patient. The term 'prophylactic' is used to encompass the use of a polypeptide or formulation described herein which either prevents or reduces the likelihood of cancer in a patient or subject.

As discussed above, the term 'effective amount' is used herein to describe concentrations or amounts of compounds according to the present invention which may be used to produce a favourable change in a disease or condition treated, whether that change is a remission, a favourable physiological result, a reversal or attenuation of a disease state or condition treated, the prevention or the reduction in the likelihood of a condition or disease state occurring, depending upon the disease or condition treated. Where agents of the invention are used in combination, each of the agents may be used in an effective amount, wherein an effective amount may include a synergistic amount.

A still further aspect of the invention provides an agent according to the first aspect of the invention in the preparation of a medicament for inhibiting the proliferation of cancer cells.

Advantageously, the cancer cells (carcinoma cells) are epithelial cells. Alternatively, the cancer cells may be squamous cells.

Conveniently, the cancer cells are selected from the group consisting of cancer cells of the breast, bile duct, brain, colon, stomach, reproductive organs, lung and airways, skin, gallbladder, liver, nasopharynx, nerve cells, kidney, prostate, lymph glands and gastrointestinal tract.

Preferably, the cancer cells are breast cancer cells. More preferably, the breast cancer cells are Elston grade III cells. Most preferably, the breast cancer cells are metastatic.

A sixth aspect of the invention provides a method for detecting cancer cells in a patient, the method comprising the following steps:
(a) providing a sample of cells from a patient to be tested;
(b) measuring the amount of hCAP18/LL-37 produced by the cells (either directly or indirectly); and
(c) comparing the amount of hCAP18/LL-37 measured in step (b) with the amount of hCAP18/LL-37 produced by healthy cells wherein elevated levels of hCAP18/LL-37 production in the sample of cells from a patient compared to the levels in healthy cells indicates that the cells are cancer cells.

Thus, the method provides a method for diagnosing cancer in a patient.

In a preferred embodiment, the cells in step (a) is selected from the group consisting of cells of the breast, bile duct, brain, colon, stomach, reproductive organs, lung and airways, skin, gallbladder, liver, nasopharynx, nerve cells, kidney, prostate, lymph glands and gastrointestinal tract.

For example, the sample of cells in step (a) may be from a tumour or from tissue suspected of being a tumour.

Preferably, step (b) comprises contacting the sample of cells with an agent that binds to hCAP18/LL-37 and then detecting the amount of hCAP18/LL-37 bound thereto.

Methods suitable for the detection of a protein in a sample are well known in the art, for example radioimmunoassays and ELISAs.

Advantageously, the agent that binds to hCAP18/LL-37 is an antibody or antigen-binding fragment thereof.

In one embodiment, step (b) comprises (i) contacting the cells with an agent that binds to hCAP18/LL-37 and (ii) detecting the amount of the hCAP18/LL-37 that binds to the agent using an antibody or antigen-binding fragment thereof. For example, step (b) may be performed by ELISA.

In an alternative embodiment, step (b) comprises measuring the amount of hCAP18/LL-37 mRNA in the cells. Suitable methods are well lnown in the art (for example see *Molecular Cloning: a Laboratory Manual,* 3rd edition, Sambrook & Russell, 2001, Cold Spring Harbor Laboratory Press).

Conveniently, step (b) is performed by Southern blot or RT-PCR.

A seventh aspect of the invention provides a method for monitoring the progression of cancer in a patient, the method comprising:
(a) providing a sample of cells collected from the patient at a first time point and detecting cancer cells therein using a method according to the sixth aspect of the invention;
(b) providing a sample of cells collected from the patient at a second time point and detecting cancer cells therein using a method according to the sixth aspect of the invention; and
(c) comparing the number of cancer cells measured in steps (a) and (b)

wherein an increased number of cancer cells measured in step (b) compared to step (a) is indicative of a progression of the cancer.

A further aspect of the invention provides a diagnostic kit for performing a method according to the sixth aspect of the invention comprising an agent that binds to hCAP18/LL-37 or to hCAP18/LL-37 mRNA.

In a preferred embodiment, the kit comprises an antibody or antigen-binding fragment thereof capable of binding to hCAP18/LL-37 (see above). The kit may further comprise a secondary antibody capable of binding to such a primary antibody, e.g. for use in an ELISA.

In an alternative embodiment, the kit comprises an oligonucleotide capable of hybridising selectively to hCAP18/LL-37 mRNA. Preferably, the oligonucleotide comprises or consists of a fragment of the nucleotide sequence of SEQ ID NO:1 or a variant thereof. It will be appreciated that the probe should be capable of hybridising selectively to hCAP18/LL-37 mRNA under high stringency conditions. Advantageously, the kit comprises a pair of primers suitable for PCR amplification of hCAP18/LL-37 mRNA.

The design of PCR primers and other hybridisation probes capable of hybridising selectively to a target mRNA, and methods of use thereof, is well known in the art, for example see Sambrook & Russell, supra.

In a preferred embodiment, the agent that binds to hCAP18/LL-37 and/or is capable of hybridising selectively to hCAP18/LL-37 mRNA comprises a detectable moiety.

By "detectable" we include single atoms and molecules that are either directly or indirectly involved in the production of a detectable species. Suitable detectable moieties are well known in medicinal chemistry and the linking of these moieties to polypeptides and proteins is well known in the art. Examples of detectable moieties include, but are not limited to, the following: radioisotopes (e.g. $^{3}$H, $^{14}$C, $^{35}$S, $^{123}$I, $^{125}$I, $^{131}$I, $^{99}$Tc, $^{111}$In, $^{90}$Y, $^{188}$Re), radionuclides (e.g. $^{11}$C, $^{18}$F, $^{64}$Cu), fluorescent labels (e.g. FITC, rhodamine, lantlianide phosphors, carbocyanine), enzymatic labels (e.g. horseradish peroxidase, β-galactosidase, luciferase, alkaline phosphatase), chemiluminescent, biotinyl groups and predetermined polypeptide epitopes recognised by a secondary reporter (e.g. leucine zipper pair sequences, binding sites for secondary antibodies, metal binding domains, epitope tags). In some embodiments, labels are attached by spacer arms of various lengths to reduce potential steric hindrance.

Preferably, the diagnostic kit comprises, in an amount sufficient for at least one assay, the diagnostic agent as a separately packaged reagent. Instructions for use of the packaged reagent are also typically included. Such instructions typically include a tangible expression describing reagent concentrations and/or at least one assay method parameter such as the relative amounts of reagent and sample to be mixed, maintenance time periods for reagent/sample admixtures, temperature, buffer conditions and the like.

Preferred aspects of the invention are described in the following non-limiting examples, with reference to the following figures:

FIG. 1—hCAP18/LL-37 is Highly Expressed in Breast Cancer.

(a) Section of ductal breast carcinoma grade III (patient no 7, Table 2) demonstrating strong immunoreactivity for hCAP18 protein in tumour cells (red precipitate) surrounding a stromal island (st). (b) In situ hybridisation shows a matching signal for hCAP18 mRNA in a section from the same tissue. Intense autoradiographic signals appear as white grains under dark-field illumination. (c) High-power view of carcinoma cells demonstrates strongly immunoreactive cells adjacent to tumour cells devoid of immunoreactivity. (d) hCAP18 immunoreactive breast carcinoma cells within a blood vessel. (e) Immunoabsorption with cathelin recombinant peptide completely abolished the hCAP18 immunoreactivity (same tissue as FIG. 1a). (f) Regular immunostaining for hCAP18 as positive control during immunoabsorption (same tissue as FIG. 1a). (g) Normal mammary gland epithelium shows weak immunoreactivity for hCAP18. Photomicrographs (a, c-g) show results obtained with the hCAP18 antibody at 1:500 dilution. Scale bars (a, b)=100 μm; (c, d)=25 μm; (e, f g)=10 μm.

Figure 2:
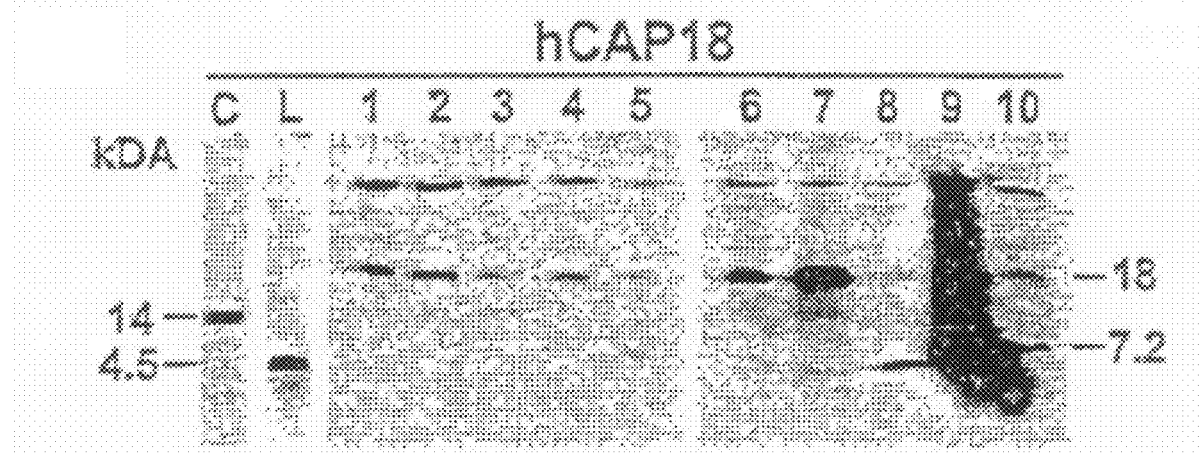

FIG. 2—hCAP-18/LL-37 is Detected by Immunoblotting in Breast Cancer.

Clinical data of patients are presented in Table 2 (sample 1-10). Recombinant cathelin (C) and LL-37 peptide (L) were used as size references. Normal breast tissue is presented in lane 1. Elston grade I tumours are presented in lanes 2, 4 and 5. A grade II tumour is presented in lane 3 and grade III tumours are presented in lanes 6-10. In all tissues there were inmmunoreactive bands corresponding to the intact non-processed 18 kDa holoprotein. The processed LL-37 peptide (4 kD) was visible in 4 of the 5 grade III tumours (no 7-10).

Figure 3:
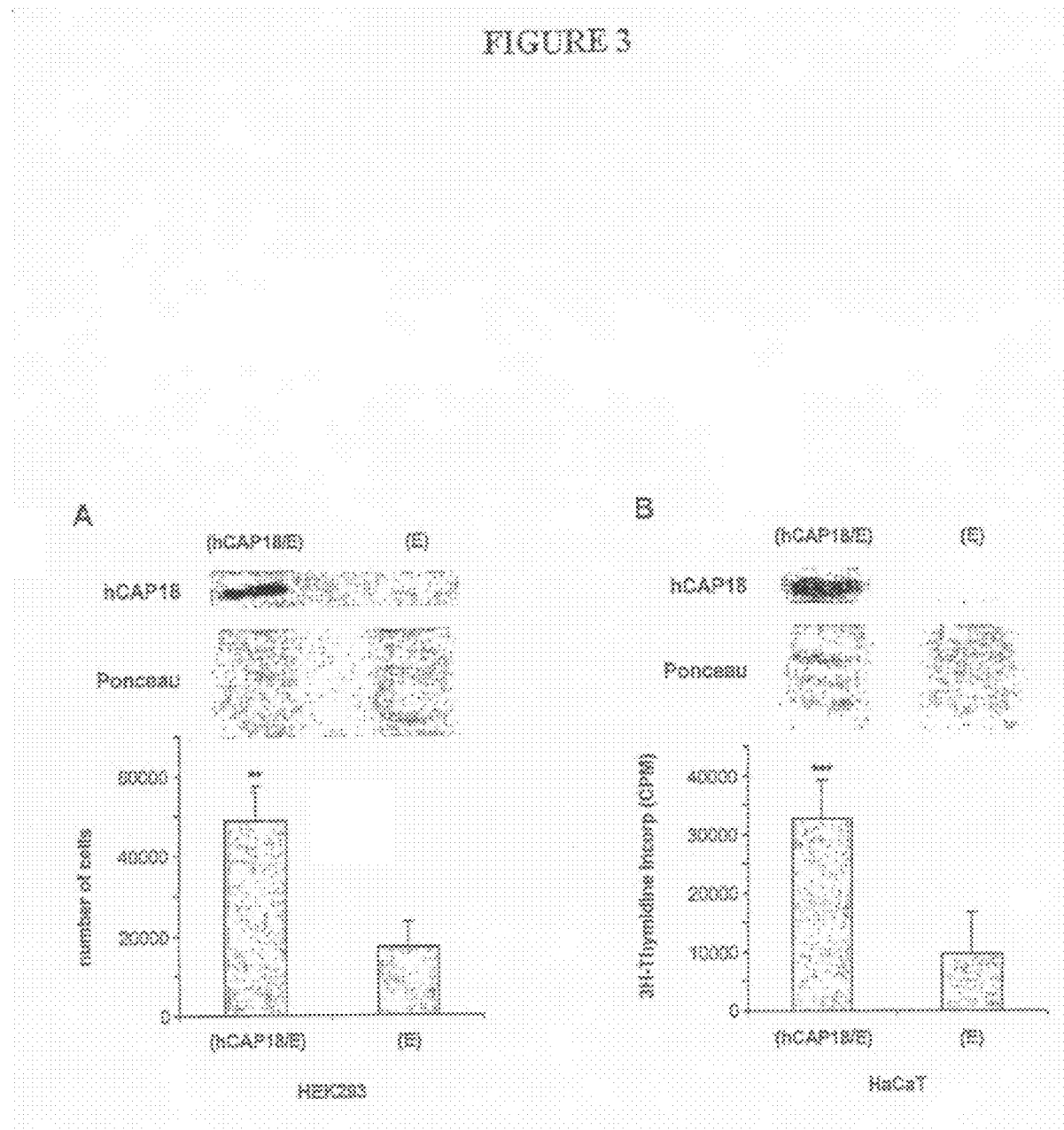

FIG. 3—Transgenic Expression of hCAP18 in Epithelial Cells Increases Cell Proliferation.

(a) Upper panel, left lane; Immunoblotting on HEK293 extracts with anti-LL37 antiserum. Cells transfected with a bicistronic vector hCAP18+EGFP (hCAP18/E) show hCAP18 protein expression. Upper panel, right lane; HEK293 cells transfected with only EGFP (E). Lower panel; HBEK293 cells (hCAP18/E) demonstrate significantly higher proliferation rate (evaluated with Flow-Cytometry) compared with control cells (E). Ponceau staining is shown as loading control. (b) Upper panel, left lane; HaCaT cells transfected as described in (a). Lower panel; hCAP18 transfected HaCaT cells demonstrate significantly higher proliferation rate (evaluated with 3H-Thymidine incorporation) compared with control cells.

Figure 4:
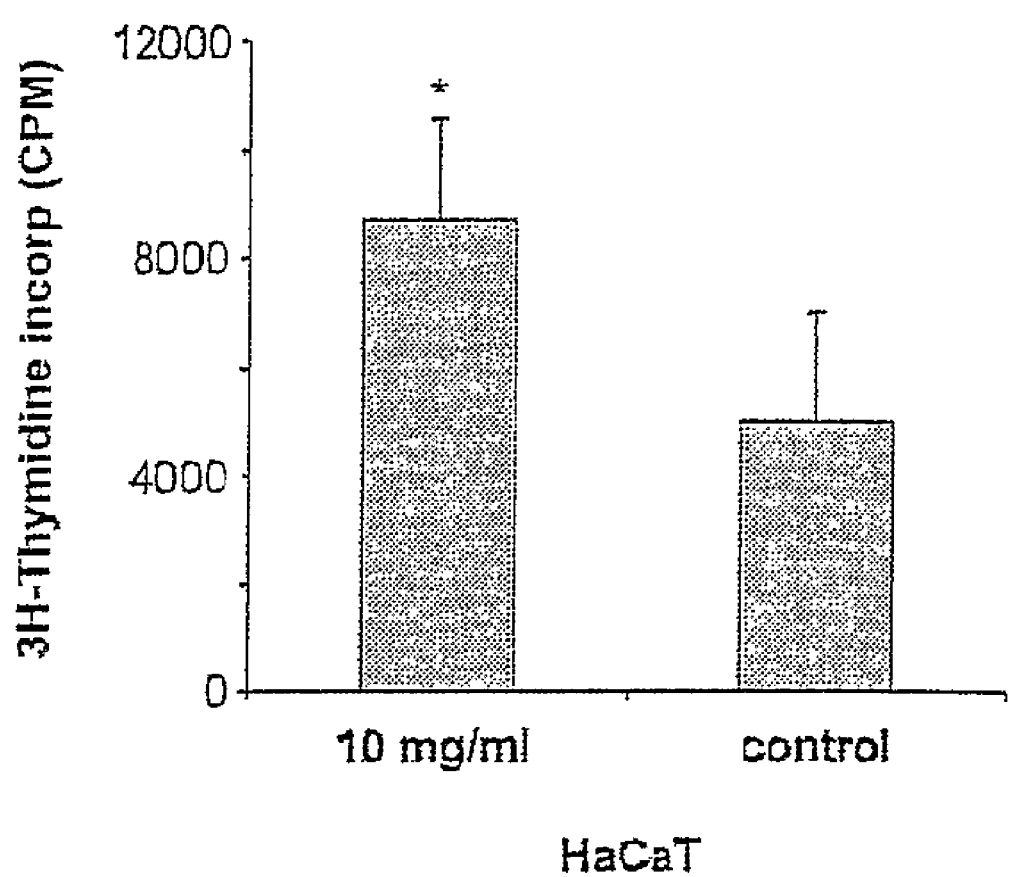

FIG. 4—Treatment with Synthetic LL-37 Peptide Increases Cell Proliferation of Epithelial Cells.

HaCaT cells synchronized by serum starvation for 72 hours and then treated for 36 hours with 10 μg/ml of synthetic, biologically active LL-37 peptide (in DMEM+5% FCS+ PEST) show significantly increased cell proliferation compared with non treated (control) HaCaT cells. Proliferation rate evaluated with [$^{3}$H]-Thymidine incorporation.

FIG. 5—The LL-37 Receptor FPRL1 is Expressed in Breast Cancer and in Normal Mammary Gland Epithelium.

(a) Section of ductal breast carcinoma Elston grade 2 (patient no 12, Table 2) with prominent immunoreactivity for FPRL1 receptor in tumour cells (red precipitate). (b) Section of normal mammary gland epithelium demonstrating imnmunoreactivity for FPRL1 in the ductal region (red precipitate).

Photomicrographs show results obtained with the FPRL1 antiserum at 1:400 dilution. Scale bars (a)=50 μm; (b)=10 μm. (c) Immunoblotting revealed that the LL-37 receptor, FPRL1, was expressed in both normal (N) and breast cancer (T) tissue. (d) HaCaT transfected with a bicistronic vector hCAP18+ EGFP (hCAP18/E) show significantly increased expression of FPRL1 receptor mRNA by real time PCR. HaCaT cells transfected with only EGFP (E) served as control.

Figure 6:
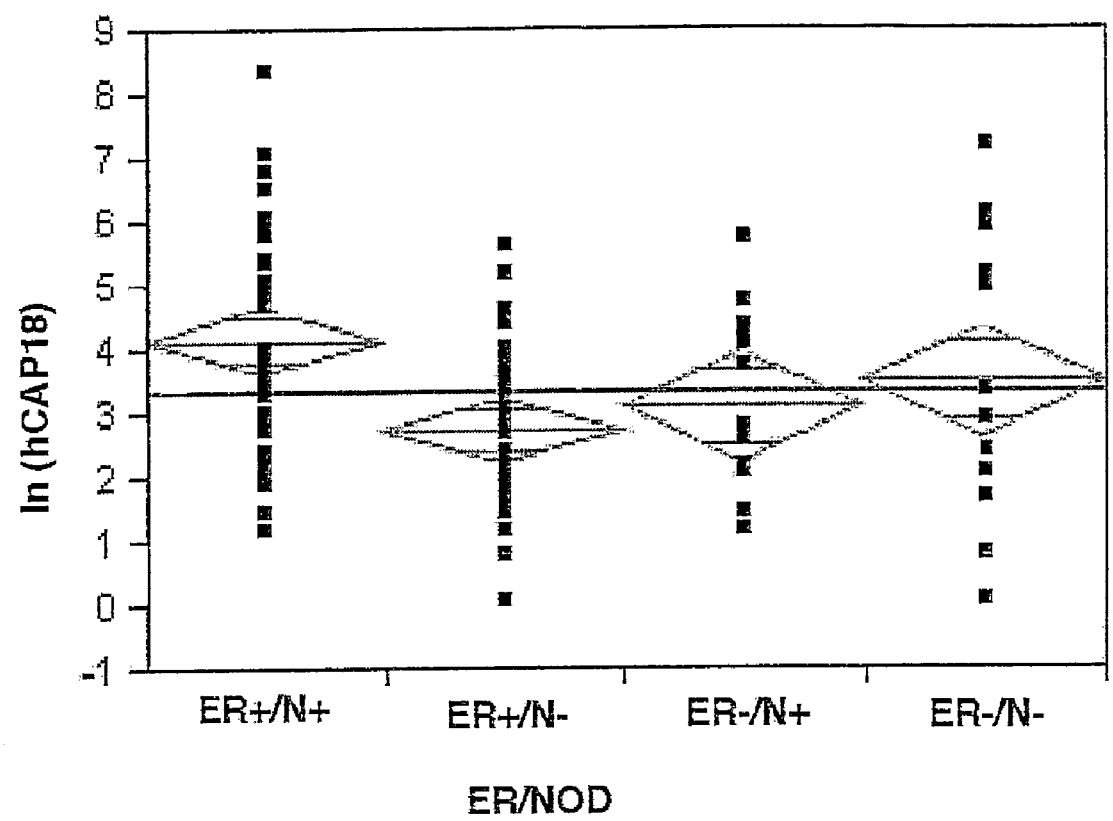

FIG. 6—Increased Expression of hCAP18/LL-37 (Displayed in Logarithmic Scale) in Estrogen Receptor (ER) and Lymph Node (N) Positive Breast Tumours.

RNA was extracted from 140 breast tumours and from 4 unaffected breast tissue samples and reverse transcribed using random hexamers as primers. The expression of hCAP18 transcripts was determined by real-time PCR using 10 ng of cDNA according to standard protocols. The samples were normalized by quantification of 18S-RNA. The mean expression of the unaffected samples was arbitrarily set to 1. Mean and deviation are evaluated by Anova statistics.

FIG. 7—LL-37 Inhibits Camptothecin-Induced Apoptosis in HEK Cells (A) and HaCat Cells (B)

A. Subconfluent cells were treated 24 hours with different LL-37 (1, 2 and 4 μM) concentrations. Cells treated with medium alone were used as control cells (a) The cells were then further cultured for 24 hours in absence (a to d) or in presence (e to h) of 6 μM camptothecin. Harvested cells were processed with a two colour apoptosis assay and flow cytometry and categorized by quadrant analysis according with fluorescent intensity as viable (not or little fluorescensce), apoptotic (positive for FL-1 YOPRO dye) and necrotic (positive for both FL-1 and PI fluorescence). The figure shows a representative of three independent experiments each performed by triplicates.

B. Quantitative analysis of apoptotic cells.

Figure 8:
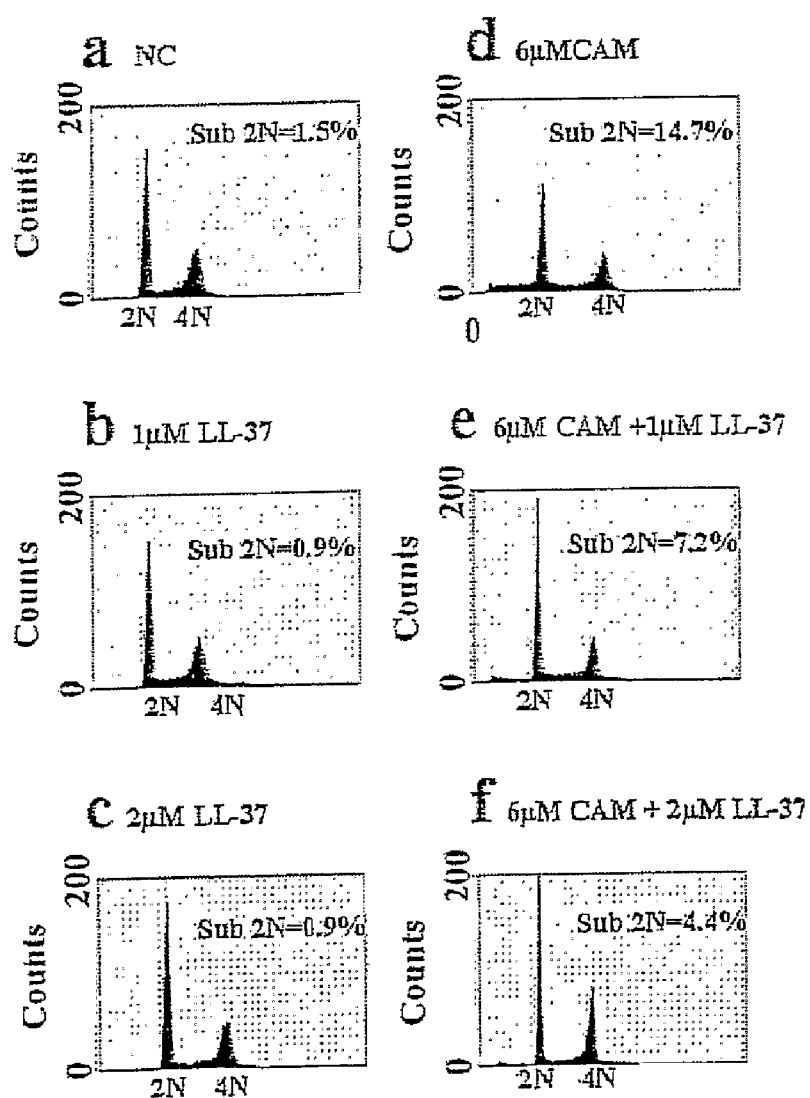

FIG. 8—Flow Cytometry Analysis of HEKn Cells Showing that Pretreatment of HIEKn Cells with LL-37 Protects from Camptothecin-Induced Apoptosis Cells treated with 1 or 2 μM of LL-37 for 24 hours (b, c, e, f) and untreated cells (a, d) were induced to undergo apoptosis by camptothecin treatment (d-f) for 24 hours. Cells were then analyzed by flow cytomety to detect non-apoptotic (2N to 4N) and apoptotic populations (sub 2N). Graphs are representative results from 3 experiments each performed in triplicate.

Figure 9:
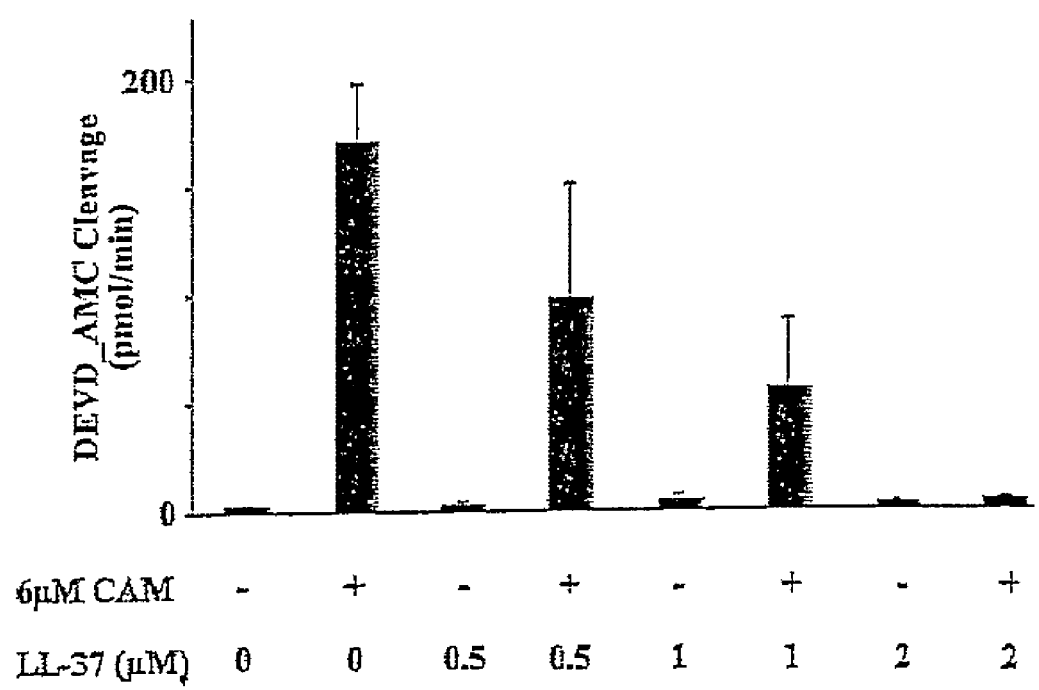

FIG. 9—LL-37 Reduces Camptothecin Activation of Caspase-3 in HEKn Cells

The cells were cultured in the presence or absence LL-37 and camptothecin and then harvested and analysed for caspase-3 activity by in vitro hydrolysis of VDVAD-AMC. Caspase activation induced by incubation for 24 hours with camptothecin was reduced by treatment the cells with LL-37. Values are means of three different experiments, each performed by triplicate.

Figure 10:
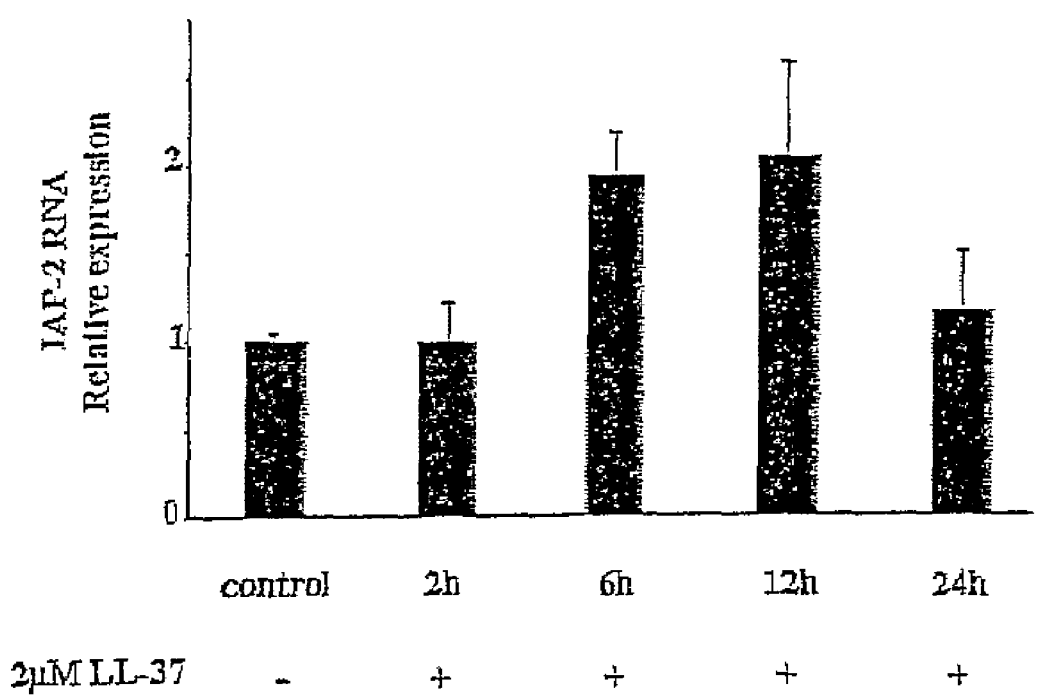

FIG. 10—LL-37 Treatment Increases the Expression of IAP2

HEKn cells were treated with 2 μM LL-37 and harvested at different time points after stimulation. RNA from these cells was reverse transcribed and the expression of IAP-2 was determined by real-time PCR. The transcription level of IAP-2 for each time point is shown normalized against 18S RNA and relative to the untreated cells (control set as 1 for each time point).

Figure 11:
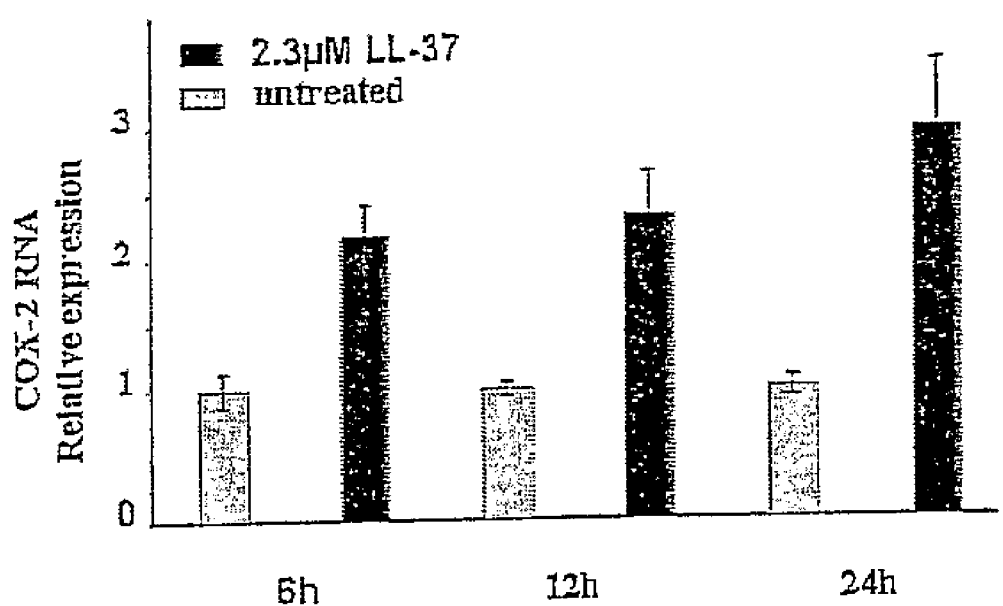

FIG. 11—LL-37 Increases the Prostaglanding Endoperoxide Synthase-2 (COX-2) Expression in HEK Cells HEKn cells were treated with 2 μM LL-37 and harvested at 6, 12 and 24 hours after stimulation. Untreated cells were used as a control in each time point (light grey columns). RNA from these cells was reverse transcribed and the relative expression of COX-2 with respect to the control was determined by qPCR as above.

Figure 12:
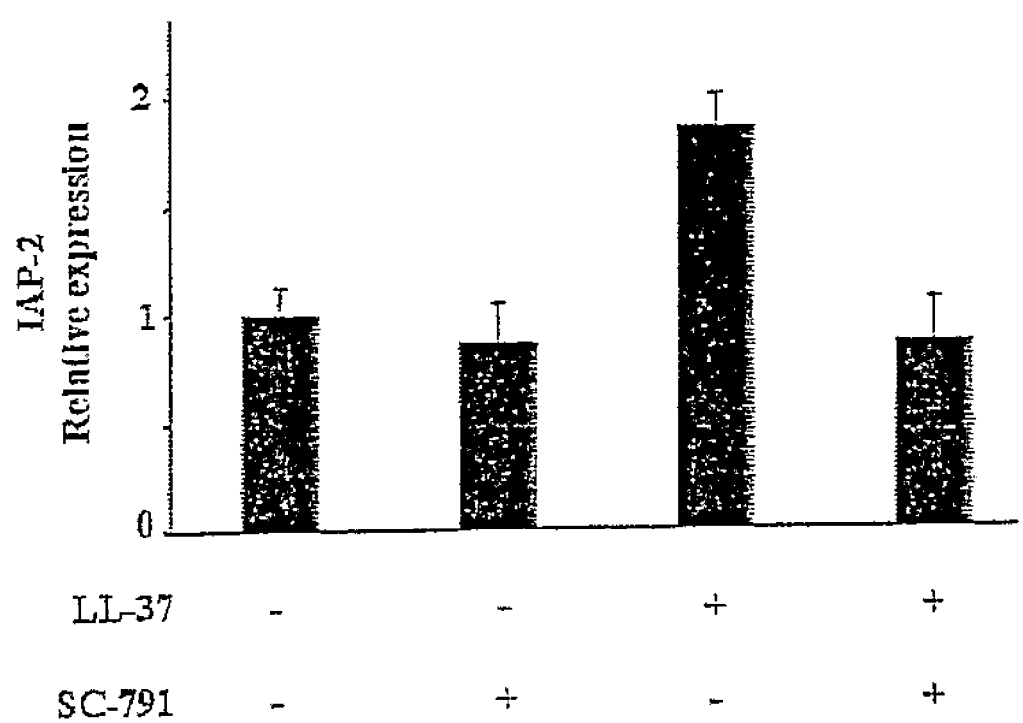

FIG. 12—COX-2 Inhibition Counteracts the LL-37 Induced Increase of IAP-2

HEKn cells were treated with or without the specific COX-2 inhibitor SC-791 (25 nM) and further incubated for 6 hours with or without LL-37 (2 μM). Levels of IAP-2 mRNA gene were analyzed by RT-PCR and are displayed relative to the untreated control sample.

EXAMPLES

Example A

The Antimicrobial Protein hCAP18/LL-37 is Highly Expressed in Breast Cancer and is a Putative Growth Factor for Epithelial Cells Introduction In this example, the expression pattern of hCAP18/LL-37 in a series of breast carcinomas is investigated, demonstrating a marked upregulation of hCAP18 mRNA and protein in the tumour cells but not in the adjacent stroma. Interestingly, the highest levels of hCAP18 protein were detected among tumours with the highest histologic grade, whereas hCAP18 levels in some low grade tumours equalled those detected in the normal breast tissue. These findings clearly contrast with the hypothesised antitumour effect that has been proposed for antimicrobial peptides, but are consistent with recent findings which suggest a role for hCAP18/LL-37 in epithelial repair and angiogenesis [5, 10]. Further supporting hCAP18/LL-37 as a growth promoting factor, we here demonstrate that proliferation of epithelial cells was significantly enhanced both by treatment with synthetic biologically active LL-37 peptide and by transgenic expression of hCAP18.

Material and Methods

Tissues

Frozen tumour tissue from 28 breast cancer patients was obtained from the Department of Pathology, Danderyd Hospital, Stockholm, Sweden (Table 2). The tumours were scored according to Elston and Ellis I-III, following established guidelines[13]. Cyclin A was used as proliferation marker (Nova-Castra Laboratories, Newcastle upon Tyne, UK). Estrogen receptor status was assessed on routinely processed paraffin sections. Uninvolved mammary tissue from eight patients with breast cancer and from two healthy individuals undergoing reductive breast surgery served as controls. All samples were examined by the same pathologist (B.S.) and classified as normal (Table 2). Written, informed consent was given by all patients. The study was approved by the Regional Committee of Ethics.

In Situ Hybridisation for hCAP18

A 435-bp hCAP18 full-length cDNA subcloned into pBluescript was used to in vitro transcribe [$^{35}$S]-labelled antisense and sense probes and in situ hybridisation was performed essentially as described[8] on samples 0-17 (Table 2).

Immunohistochemistry

Immunohistochemistry was performed on samples 0-17 (Table 2). Cathelin-affinity-purified rabbit antiserum against recombinant hCAP18[14] was used at 1:500 dilution as earlier described[10] according to the indirect peroxidase method using a Vectastain kit (Vector Laboratories, Burlingame, USA). To ascertain the specificity of the staining, immunoabsorption was performed as earlier reported[10]. For detection of the FPRL1 receptor, affinity-purified goat polyclonal antibody was used at 1:400 dilution (Santa Cruz Biotechnology, Santa Cruz, Calif.) according to the indirect peroxidase method.

Protein Extraction and Western Blot Analysis

Frozen tumour tissues, 16-60 mg, were homogenised in lysine buffer using an electric homogeniser. Proteins from tumour tissues and cell lines were extracted in SDS-containing sample buffer according to standard protocols[15]. The protein concentration was determined by a spectrophotometric assay and adjusted with SDS-containing sample buffer to equal protein concentration[16]. For the detection of hCAP18/LL-37 the extracts were separated on 16.5% Tris-Tricine Ready gels (Bio-Rad Laboratories, Hercules, Calif.). Recombinant cathelin[17] and synthetic LL-37 peptide were used as size references. For the detection of ERK1/2 and FPRL1, protein was separated on 12% and 8% Tris-Glycine gels respectively. To confirm that approximately equal amounts of protein in each sample were blotted, the filters were reversibly stained with a 3% Ponceau S solution (Sigma Aldrich, USA) in 3% TCA, before incubating with the primary antibody. Affinity purified anti-cathelin antiserum[17], affinity-purified anti-LL-37 antiserum[10], anti-FPRL1 antiserum (sc18191, Santa Cruz Biotechnology, Calif.) and monoclonal anti-ERK1/2 antibody (Cell Signaling Technology, Beverly Mass.) were all used at 1:1000 dilution. After electroblotting onto nitrocellulose filters (Schleicher & Schuell, Dassel, Germany), and sequential incubation with primary antibodies and horse-radish-peroxidase conjugated IgG (Santa Cruz Biotechnology, Santa Cruz, Calif.), signals from enhanced chemiluminiscence (ECL, Amersham Biosciences, Piscataway, N.J.) were captured with a CCD camera (LAS 1000, Fujifilm, Tokyo, Japan).

ELISA

A sandwich ELISA previously described[17] was used to quantify hCAP18 in protein extracts from normal mammary gland and tumour tissues.

Expression Analysis of hCAP18 by Real-Time PCR

RNA from four normal samples and four tumours was extracted with the Qiagen RNeasy kit (Operon Biotechnologies, Cologne, Germany) and reverse transcribed with a first strand synthesis kit (Amersham Biosciences, Norwalk, Conn.). RNA was quantified by Real-Time PCR on an ABI Prism 7700 (Applied Biosystems) using 10 ng of cDNA according to standard protocols. The samples were evaluated in triplicates. Sequences were 5'-GTCACCAGAGGATTGT-GACTTCAA-3' [SEQ ID NO:2] and 5'-TTGAGGGTCACT-GTCCCCATA-3' [SEQ ID NO:3] for the primers, and 6-FAM-5'-CCGCTTCACCAGCCCGTCCTT-3'-BHQ1 [SEQ ID NO:4] for the fluorigenic probe. The samples were normalised by quantification of 18S-RNA (Assay on Demand, Applied Biosystems). The mean expression of the normal samples was arbitrarily set to 1.

Synthetic LL-37 Peptide

LL-37 peptide was synthesised and purified by HPLC to a purity of 98% (PolyPeptide Laboratories A/S, Hillerød, Denmark). Biological activity of the peptide was confirmed in an antibacterial assay[18].

LL-37 Peptide Treatment of Epithelial Cells

A spontaneously immortalised human keratinocyte cell line (HaCaT)[19] was cultured in DMEM (Dulbecco's modified Eagle's medium, Gibco BRL, Life Technologies, Scotland) supplemented with 10% FCS (fetal calf serum, Hy-Clone, Boule Nordic AB Huddinge, Sweden) and antibiotics (PEST=penicillin 50 U/l and streptomycin 50 mg/ml, Gibco BRL). Cells were harvested at 70% confluence and seeded in 96-well plates, 2000 cells in 100 µl medium (DMEM+10% FCS and PEST). After 12 hours, medium was changed to serum free medium (DMEM+PEST) and cells were synchronized in G0/G1 by serum starvation for 72 hours and then treated with 100 µl of medium (DMEM+5% FCS+PEST) containing synthetic biologically active LL-37 peptide at 10 µg per ml. Cells treated with only DMEM+5% FCS and PEST served as control. The experiments were performed in quadruplicates. Cell proliferation was evaluated by [$^3$H]-Thymidine incorporation. Cells were treated with 1 µCi/well of [$^3$H]-Thymidine (20.00 Ci/mmol, Perkin Elmer Life Sciences Inc. Boston, Mass.) during 12 hours and harvested (Harvester 96, Tomtec, Orage, Conn.) onto a glass fiber filter (Wallac Oy Turku, Finland). The incorporation of [$^3$H]-Thymidine was determined using a liquid scintillation counter (Microbeta Pluss, Wallac Sveriges AB). The experiment was repeated twice in 6 replicates.

Transgenic Expression of hCAP18 in HEK293 and HaCaT Cells

A Bfa1 fragment from Image clone 3057931[20] containing the entire coding sequence including the 16 bp of the 5'-untranslated region, was subcloned into the Sma1-site of the bycistronic vector pIRES2-EGFP (BD Biosciences, Bedford, Mass.). HEK293 and HaCaT cells were transfected using Fugene (Roche Diagnostics, Indianapolis, Ind.) under standard conditions, and selected for two weeks with 400 ng/ml G418 (Invitrogen, Paisley, UK). Cells were sorted for EGFP expression with a MoFlo® high speed cell sorting flow cytometer (DakoCytomation, Fort Collins, Colo.) using Summit™ software for data analysis, and their expression of CAP18 was quantified by immunoblotting. Control cell lines were similarly established by transfection with the vector expressing EGFP only. The cell lines maintained a stable expression of CAP18 during several months of continued cultivation without any selection. The experiment was repeated twice in 30 replicates.

Proliferation Assays for HEK293 and HaCaT Cells Stably Transfected with hCAP18

HEK293 cells transfected with hCAP18 were harvested at 70% confluence and seeded in 24-well plates. After 24 hours, medium was changed and cells were cultured in 2 ml of medium (Optimem, Gibco BRL, Life Technologies, Scotland) supplemented with 5% FCS and PEST. Cells were harvested at day 6 and counted by flow cytometry (Becton Dickinson, Bedford, Mass.). Cell viability was measured with Trypan Blue; under all conditions less than 5% of the cells were Trypan Blue positive. All conditions were performed in triplicates. HEK293 cells transfected with the vector expressing only EGFP served as control.

HaCaT cells transfected with hCAP18 were harvested at 70% confluence and seeded at 2000 cell per well in 96 well plates in DMEM with 10% FCS+PEST. Medium was changed 12 hours later to DMEM supplemented with 5% FCS+PEST. After 24 hours of culture, the cells were treated 12 hours with 1 µCi/well of [$^3$H]-Thymidine, harvested and analysed as described above. HaCaT cells transfected with the vector only expressing EGFP served as control.

Expression Analysis of FPRL1

RNA fiom HaCaT cells was extracted with the RNeasy kit (Qiagen) and reverse transcribed with a first strand synthesis kit (Amersham-Pharmacia). FPRL1 RNA was quantified by Real-Time PCR and normalized against 18S-RNA as described above. Sequences were 5'-TCTGCTGGCTA-CACTGTTCTGC-3' [SEQ ID NO:2] and 5'-GACCCCGAG-GACAAAGGTG-3' [SEQ ID NO:3] for the primers, and 6-FAM-5'-CCCAAGCACCACCAATGGGAGGA-3'-BHQ1 [SEQ ID NO:4] for the fluorigenic probe.

Pertussis Toxin Assay

To assess the involvement of FPRL1 in mediating the stimulation of epithelial cell proliferation induced by hCAP18/LL-37, HaCaT cells were treated with the G-protein-coupled receptor inhibitor pertussis toxin. Cells were preincubated with pertussis toxin (Sigma-Aldrich, Switzerland) 24 h before the LL-37 treatment in a final toxin concentration of 20 ng/ml. Medium was changed 48 hours after cell seeding and the HaCaT cells were treated with 100 µl of medium (DMEM+5% FCS and PEST) containing synthetic biologically active LL-37 peptide at 5 or 10 µg per ml respectively. Cells treated with only DMEM+5% FCS and PEST served as control.

Assay of Phosphorylated ERK1/2 in LL-37 Treated HaCaT Cells

HaCaT cells were seeded at 10% confluence and kept in DMEM with 0.2% FCS for 36 hours. For the next 48 hours, cells were cultured in DMEM with 1% or 5% FCS respectively, and in presence or absence of LL-37 at 10 µg/ml, with daily changes of medium. EGF at 10 ng/ml served as positive control. The expression of phosphorylated ERK 1/2 was evaluated by Western blot analysis with a mouse monoclonal antibody (Cell Signaling Technology, Beverly Mass.).

Statistical Analysis

Values are presented as mean number of cells or counts per minute (CPM) plus or minus SD. Comparisons between groups were analysed by two-sided t-tests.

Results were considered statistically significant for P values <0.05. For the analysis of the expression in tumours, a one-tailed t-test was performed on hCAP18 protein levels at a significance level of <0.05.

Results hCAP18/LL-37 is Expressed in Breast Cancer

Patient details are presented in Table 2.

By in situ hybridisation, there was low signal for hCAP18 mRNA (not shown) and weak immunoreactivity for HCAP18 protein in breast tissue from a healthy control (FIG. 1g) and in uninvolved breast cancer (not shown). All breast cancer tissues showed immunoreactivity for hCAP18 in the tumour cells and not in the stroma (FIG. 1a, c, d). The tumour cell population was not homogenous with regard to hCAP18 immunoreactivity, strongly positive cells being found adjacent to cells devoid of detectable hCAP18 (FIG. 1c). Immunoabsorption with cathelin recombinant protein abolished the hCAP18 immunoreactivity (FIG. 1e, f). By in situ hybridisation, positive signal for hCAP18 mRNA was detected in the same areas closely matching the expression pattern obtained with immunohistochemistry (FIG. 1b). Signal intensity varied and was most prominent among high grade tumours. Control sections hybridised with the sense hCAP18 cRNA probe lacked specific signal for hCAP18 mRNA (not shown).

Quantification of hCAP18 protein by ELISA in breast cancer tissue extracts revealed no difference between Elston I and II grade tumours, but clearly higher hCAP18 levels in tumours of the highest malignancy grade (Table 2). The difference between Elston III grade and the remaining tumours was statistically significant ($p<0.01$). Ten of the 13 grade III tumours reached or exceeded a hCAP18 concentration of 5 ng/mg total protein. Only 2 of the remaining 18 tumour samples reached this level. We also assayed four specimen of healthy breast tissue which revealed similar levels as Elston I or II tumours. To verify the expression pattern obtained by ELISA, we performed Real-Time PCR on four normal samples and on four of the tumours. The results of transcript quantification were in line with the data on protein expression (Table 2).

By immunoblotting, all tumours and normal breast tissues investigated showed immunoreactive bands corresponding to the intact non-processed 18 kDa holoprotein (FIG. 2). In 4 of the 5 investigated grade III tumours (Table 2, sample 6-10), we also detected bands corresponding to LL-37, the processed hCAP18 protein (FIG. 2). The antiserum used is raised against the hCAP18 holoprotein and detects LL-37 at high concentrations even though it is affinity purified against the cathelin peptide[10].

hCAP18/LL-37 Increases Proliferation of Epithelial Cells

HEK293 and HaCaT cells transfected with a hCAP18 (hCAP18/E) expression vector demonstrated significantly higher proliferation rate than control cells transfected with the vector expressing EGFP only (E) (FIGS. 3A and B). By immunoblotting of protein extracts from the transfected HEK293 and HaCaT cells, we confirmed that these hCAP18 vector-containing cells produced the holoprotein (FIGS. 3A and B) and a 4 kD immunoreactive band corresponding to LL-37 was detected in the cell medium (data not shown). In addition, HaCaT cells cultured at 5% fetal calf serum and treated with synthetic biologically active LL-37 peptide at 10 µg/ml demonstrated a significant increase in cell proliferation (FIG. 4).

TABLE 2

| Sample[a] (no) | Age (year) | Type | Grading[b] | ER[c] | Cyclin A[d] | IH & ISH[e] | hCAP18[f] (ng/mg) | Real Time PCR[g] | Treatment[h] | Axillar LN[i] | Clinical Status[j] |
|---|---|---|---|---|---|---|---|---|---|---|---|
| 0 | 30 | Healthy | | | | • | | | | | |
| 1 | 72 | Healthy | | | | • | 0.7 | | | | |
| 2 | 53 | Lobular | I | + | L | • | 2.3 | | M, TAM | − | 0 |
| 3 | 65 | Ductal | II | + | H | • | 1.1 | | M, CT | − | CIS |
| 3b | | Normal | | | | • | | | | | |
| 4 | 37 | Ductal | I | + | H | • | 2.3 | | PM, Rx, TAM | − | 0 |
| 5 | 69 | Colloid | I | + | L | • | 1.7 | | PM, Rx, TAM | − | 0 |
| 6 | 84 | Ductal | III | − | H | • | 5.4 | | M | − | † |
| 7 | 53 | Ductal | III | − | H | • | 35.8 | | M, Rx, CT | + | 0 |
| 8 | 55 | Ductal | III | − | H | • | 5 | 8 | PM, Rx, CT | + | Metastasis |
| 9 | 73 | Ductal | III | − | H | • | 11.8 | | M, TAM | − | † |
| 10 | 47 | Ductal | III | − | H | • | 5.3 | | M, CT, Rx | − | † |
| 11 | 64 | Ductal | II | + | H | • | 1.6 | | M, Rx, TAM | − | 0 |
| 12 | 52 | Ductal | II | + | H | • | 5 | | PM, Rx, CT | + | 0 |
| 12b | | Normal | | | | • | | | | | |
| 13 | 69 | Ductal | I | + | L | • | 0.9 | | PM, Rx, TAM | + | 0 |
| 14 | 31 | Ductal | II | + | L | • | 4 | | M, Rx, CT | + | 0 |
| 14b | | Normal | | | | • | | | | | |
| 15 | 58 | Ductal | I | + | L | • | 3.9 | | PM, Rx, TAM | − | 0 |
| 16 | 70 Right | Ductal | I | + | L | • | 4.12 | | PM, Rx, TAM | − | 0 |
| 16 | Left | Lobular | II | + | L | • | 4.56 | | M, TAM | − | 0 |
| 16b | | Normal | | | | • | | | | | |
| 17 | 70 | Tubular | I | + | L | • | | | M, Rx, TAM | − | 0 |
| 18 | 76 | Ductal | I | + | L | | 3.9 | | M, Rx, CT | + | 0 |
| 19 | 64 | Ductal | III | + | H | | 3.9 | | PM, Rx, CT | − | 0 |
| 20 | 69 | Ductal | I | + | L | | 4.7 | | PM, Rx, TAM | − | 0 |
| 21 | 78 | Lobular | III | + | H | | 38 | | M, CT | + | 0 |
| 22 | 67 | Ductal | III | + | H | | 4.0 | | M, CT | nd | 0 |
| 23 | 82 | Colloid | I | + | L | | 11.7 | | M, CT, | nd | 0 |
| 24 | 76 | Ductal | II | − | L | | 3.7 | | M, Rx, CT | − | 0 |
| 25 | 44 | Ductal | III | + | H | | 7.0 | 11 | M, Rx, CT | + | 0 |
| 26 | 79 | Medullary | III | + | H | | 4.8 | 18 | M, Rx, CT | + | 0 |
| 27 | 66 | Ductal | I | + | L | | 8.7 | | PM, Rx, CT | − | † |
| 28 | 58 | Ductal | III | − | H | | 41 | 11 | M, Rx, CT | + | † |
| 29 | 65 | Metastasis | — | + | H | | 29.5 | | CT | + | Metastasis |
| 30 | 54 | Lobular | III | + | H | | 5.8 | | M, Rx, CT | + | 0 |
| 31 | 81 | Normal | | | | | 1.2 | 0.6 | | | |
| 32 | 60 | Normal | | | | | 2.9 | 1.1 | | | |

TABLE 2-continued

| Sample[a] (no) | Age (year) | Type | Grading[b] | ER[c] | Cyclin A[d] | IH & ISH[e] | hCAP18[f] (ng/mg) | Real Time PCR[g] | Treatment[h] | Axillar LN[i] | Clinical Status[j] |
|---|---|---|---|---|---|---|---|---|---|---|---|
| 33 | 65 | Normal | | | | | 2.9 | 1.5 | | | |
| 34 | 55 | Normal | | | | | | 1.1 | | | |

[a]Tissues from 28 patients with breast carcinoma, normal mammary tissue from 8 patients with breast carcinoma and from 2 healthy individuals undergoing reconstructive breast surgery (sample no 0 and1).
[b]Tumours graded according to Elston and Ellis.
[c]Assessment of estrogen receptor (ER) status performed with immunohistochemistry.
[d]Percentage of cells expressing proliferation marker Cyclin A. Low (L) < 5%, High (H) ≧ 5%.
[e]Tissues investigated (•) with immunohistochemistry (IH) and in situ hybridisation (ISH) for hCAP18.
[f]Protein extraction from tissues, hCAP18 levels measured with ELISA and presented as ng hCAP18 per mg total protein.
[g]RNA extraction from tissues, hCAP18 mRNA measured with Real Time PCR (TaqMan), the mean of normal arbitrarily set as one.
[h]M = mastectomy, PM = partial mastectomy, Rx = radiation, CT = chemo therapy, TAM = tamoxifene.
[i]Axillary lymph nodes status at surgery. nd = not done.
[j]Clinical status was assessed 1.5-2 years after diagnosis. † = dead, 0 = no clinical relapse, CIS = carcinoma in situ.

The LL-37 Receptor FPRL1 is Expressed in Breast Cancer

The G-protein-coupled receptor, FPRL1 has been shown to mediate LL-37 induced effects in eukaryote cells[4,5] and to assess its potential role in the present setting, we investigated the expression of FPRL1 protein in mammary tissue and found strong immunoreactivity for FPRL1 both in breast cancer cells and in normal glandular epithelium (FIG. 5a,b). Immunoblotting confirmed that FPRL1 was expressed in both tissues (FIG. 5c). In addition, transgenic expression of hCAP18 significantly increased the expression of FPRL1 mRNA (FIG. 5d) in HaCaT cells which may further support the involvement of FPRL1 in hCAP18/LL-37 signalling. However, pretreatment of HaCat cells with pertussis toxin did not abolish but suppressed the proliferation of these cells by approximately 50% (not shown), indicating that FPRL1 may not be uniquely involved in mediating hCAP18/LL-37 growth stimulatory effects in these cells. To test the possible involvement of ERK1/2 in activation of epithelial cell proliferation, we treated HaCaT cells with synthetic biologically active LL-37 but there was no significant activation of ERK1/2, which indicates that EGFR is not involved in mediating the LL-37 stimulatory effect on HaCaT cell proliferation.

Discussion

In the present study we demonstrate that hCAP18/LL-37 is constitutively produced in normal mammary gland epithelium. This is consistent with a role for LL-37 in antimicrobial barrier protection in human and agrees with earlier reports where low constitutive expression of LL-37 was found in normal quiescent epithelium, in contrast to the pronounced expression seen in association with injury and inflammation[7-10]. Constitutive expression of antimicrobial peptides has previously been detected in various exocrine glands such as the human cathelicidin LL-37 in sweat glands, the cathelicidin CRAMP in murine salivary glands and beta-defensins in human salivary glands[21-23]. Expression of human beta-defensin-2 (hBD-2) mRNA in mammary glands was reported by Bals et al in 1998 and recently other groups have found constitutive hBD-1 expression in mammary glandular tissue of non-lactating women as well as in breast tissue during lactation and in breast milk[24-26].

Our finding that hCAP18/LL-37 is expressed in breast cancer cells is novel. Interestingly, the production of hCAP18 was most notably increased in the breast epithelium of high grade tumours compared with normal mammary epithelium or low grade tumours. The hCAP18 expression was however neither universal nor uniform, i.e. not all cancer cells were positive for hCAP18, but distinctly positive cells were found adjacent to cells devoid of detectable hCAP18 mRNA and protein (FIG. 1c), and the degree of expression varied considerably among cells in all tumour types. This may reflect a complex yet strictly controlled regulation of hCAP18 as has been suggested for human alpha-defensins in renal cell carcinoma[27].

In our study, the highest hCAP18/LL-37 levels were detected among tumours with the highest histologic grade. Although the difference in hCAP18 expression between high grade tumours on the one hand and low grade and normal breast tissues is statistically significant, there is no strict correlation. Within all groups there were tumours expressing hCAP18 at the level of the healthy samples and two of the grade I tumours showed a relatively high expression otherwise only observed among the grade III tumours. However, given the limitations by the sample numbers, our observations suggest a potential correlation between degree of malignancy and expression of hCAP18/LL-37. One may argue that the overexpression of hCAP18 in breast cancer may result from failures in intracellular pathways affecting the regulation of hCAP18, and that hCAP18 expression reflects these alterations rather than providing a growth advantage for the tumour. However, coupled with the in vitro studies presented here, we believe that the data underline the potential role for LL-37 in promoting tumour growth.

The biological role of antimicrobial peptides in carcinomas is unclear. High hBD-2 protein concentration and marked immunoreactivity for both human alpha- and beta-defensins have been found in various oral carcinomas and it has been suggested that the increased levels of these antimicrobial peptides may be the result of infection and/or stimulation by cytokines[28-30]. Other studies have proposed that antimicrobial peptides isolated from insects, e.g. melittin and cecropin related peptides exert antitumour effects on mammalian tumour cells[31-34]. Moreover, vector mediated delivery and expression of the coding sequences for cecropin and mellitin in a human bladder carcinoma cell line suppressed tumourigenicity in nude mice[11]. Likewise, transgenic expression of the porcine cathelicidin PR-39, reduced the invasive capacity of human hepatocellular carcinoma[12].

Although further studies are required to elucidate the functions of antimicrobial peptides in cancer, a multifunctional role for these peptides is becoming increasingly manifest. In addition to pathogen inactivation through a direct membrane effect, LL-37 exerts chemotactic effects in vitro, inducing migration of human neutrophils, monocytes, subsets of T-cells and mast cells[4,35,36]. This chemotactic activity is dependent on binding of LL-37 to FPRL1, a pertussis toxin-sensitive, membrane bound G-protein-coupled receptor[4]. Additional suggested functions for hCAP18/LL-37 include a role in epithelial repair and angiogenesis by promoting re-epithelialization of skin wounds and neovascularization[5,10].

Thus, the marked hCAP18/LL-37 expression in breast cancer cells presented herein may reflect a growth advantage for these tumour cells. To test this hypothesis, we transfected the human epithelial cell lines HEK293 and HaCaT with an hCAP18 expression vector and found a significant increase in proliferation of transfected cells. In addition, synthetic biologically active LL-37 peptide significantly increased proliferation of HaCaT cells. These findings clearly contrast with the suggested antitumour effect proposed for antimicrobial peptides, but are consistent with recent findings by Müller et al, that human alfa-defensins may modulate progression of renal cell carcinoma (RCC). These defensins were found in tumour cells of RCC as well as in normal tubular epithelial of the kidney and at physiological concentrations stimulated tumour cell proliferation[27].

Our in vitro studies suggest that LL-37 stimulates proliferation of epithelial cells, partially through FPRL1 since blocking the receptor with pertussis toxin decreased the exogenous LL-37 proliferation effect by approximately 50%, possibly indicating the involvement also of other receptors. In a recent study it was suggested that LL-37 activates airway epithelial cells by activation of the mitogen-activated protein kinase/extracellular signal-regulated kinase (MAPK/ERK kinase=MEK) via transactivation of the epidermal growth factor receptor (EGFR)[37]. However, in our experiments we did not detect any significant activation of ERK1/2.

In conclusion, the results presented herein indicates that LL-37 promotes tumour growth.

References

1. Gudmundsson G H, Agerberth B, Odeberg J, Bergman T, Olsson B, Salcedo R. The human gene FALL39 and processing of the cathelin precursor to the antibacterial peptide LL-37 in granulocytes. Eur J Biochem 1996; 238:325-32.
2. Zanetti M, Gennaro R, Romeo D. Cathelicidins: a novel protein family with a common proregion and a variable C-terminal antimicrobial domain. FEBS Lett 1995; 374:1-5.
3. Agerberth B, Gunne H, Odeberg J, Kogner P, Boman H G, Gudmundsson G H. FALL-39, a putative human peptide antibiotic, is cysteine-free and expressed in bone marrow and testis. Proc Natl Acad Sci USA 1995; 92:195-99.
4. Yang D, Chen Q, Schmidt A P, Anderson G M, Wang J M, Wooters J, Oppenheim J J, Chertov O. LL-37, the neutrophil granule- and epithelial cell-derived cathelicidin, utilizes formyl peptide receptor-like 1 (FPRL1) as a receptor to chemoattract human peripheral blood neutrophils, monocytes, and T cells. J Exp Med 2000; 192:1069-74.
5. Koczulla R, von Degenfeld G, Kupatt C, Krotz F, Zahler S, Gloe T, Issbrucker K, Unterberger P, Zaiou M, Lebherz C, Karl A, Raake P, et al. An angiogenic role for the human peptide antibiotic LL-37/hCAP-18. J Clin Invest 2003; 111:1665-72.
6. Cowland J B, Johnsen A H, Borregaard N. hCAP-18, a cathelin/pro-bactenecin-like protein of human neutrophil specific granules. FEBS Lett 1995; 368:173-76.
7. Frohm M, Agerberth B, Ahangari G, Ståhle-Bäckdahl M, Lidén S, Wigzell H, Gudmundsson G H. The expression of the gene coding for the antibacterial peptide LL-37 is induced in human keratinocytes during inflammatory disorders. J Biol Chem 1997; 272:15258-63.
8. Frohm Nilsson M, Sandstedt B, Sørensen O, Weber G, Borregaard N, Ståhle-Bäckdahl M. The human cationic antimicrobial protein (hCAP18), a peptide antibiotic, is widely expressed in human squamous epithelia and colocalizes with interleukin-6. Infect Immun 1999; 67:2561-66.
9. Dorschner R A, Pestonjamasp V K, Tamakuwala S, Ohtake T, Rudisill J, Nizet V, Agerberth B, Gudmundsson G H, Gallo R L. Cutaneous injury induces the release of cathelicidin anti-microbial peptides active against group A Streptococcus. J Invest Dermatol 2001; 117:91-97.
10. Heilborn J D, Nilsson M F, Kratz G, Weber G, Sorensen O, Borregaard N, Stahle-Backdahl M. The cathelicidin antimicrobial peptide LL-37 is involved in re-epithelialization of human skin wounds and is lacking in chronic ulcer epithelium. J Invest Dermatol 2003; 120:379-89.
11. Winder D, Gunzburg W H, Erfle V, Salmons B. Expression of antimicrobial peptides has an antitumour effect in human cells. Biochem Biophys Res Commun 1998; 242:608-12.
12. Ohtake T, Fujimoto Y, Ikuta K, Saito H, Ohhira M, Ono M, Kohgo Y. Proline-rich antimicrobial peptide, PR-39 gene transduction altered invasive activity and actin structure in human hepatocellular carcinoma cells. Br J Cancer 1999; 81:393-403.
13. Pathology NCGfBS. Pathology reporting in breast cancer screening second edition, NHSBSP Publication 1995.
14. Sørensen O, Bratt T, Johnsen A H, Madsen M T, Borregaard N. The human antibacterial cathelicidin, hCAP-18, is bound to lipoproteins in plasma. J Biol Chem 1999; 274:22445-51.
15. Ausubel F M, Brent R, R. E. K, Moore D M, Seidman J G, Smith J A, Struhl K. Current Protocols in Molecular Biology: Wiley & Sons, Hoboken, N.J., 2003.
16. Schaffner W, Weissmann C. A rapid, sensitive, and specific method for the determination of protein in dilute solution. Anal Biochem 1973; 56:502-14.
17. Sørensen O. Cowland J B, Askaa J, Borregaard N. An ELISA for hCAP-18, the cathelicidin present in human neutrophils and plasma. J Immunol Methods 1997; 206:53-59.
18. Frohm M, Gunne H, Bergman A C, Agerberth B, Bergman T, Boman A, Lidén S, Jörnvall H, Boman H G. Biochemical and antibacterial analysis of human wound and blister fluid. Eur J Biochem 1996; 237:86-92.
19. Boukamp P, Petrussevska R T, Breitkreutz D, Hornung J, Markham A, Fusenig N E. Normal keratinization in a spontaneously immortalized aneuploid human keratinocyte cell line. J Cell Biol 1988; 106:761-71.
20. Lennon G, Auffray C, Polymeropoulos M, Soares M B. The I.M.A.G.E. Consortium: an integrated molecular analysis of genomes and their expression. Genomics 1996; 33:151-2.
21. Murakami M, Ohtake T, Dorschner R A, Gallo R L. Cathelicidin antimicrobial peptides are expressed in salivary glands and saliva. J Dent Res 2002; 81:845-50.
22. Murakami M, Ohtake T, Dorschner R A, Schittek B, Garbe C, Gallo R L. Cathelicidin anti-microbial peptide expression in sweat, an innate defense system for the skin. J Invest Dermatol 2002; 119:1090-5.
23. Sahasrabudhe K S, Kimball J R, Morton T H, Weinberg A, Dale B A. Expression of the antimicrobial peptide, human beta-defensin 1, in duct cells of minor salivary glands and detection in saliva. J Dent Res 2000; 79:1669-74.
24. Bals R, Wang X, Wu Z, Freeman T, Bafna V, Zasloff M, Wilson J M. Human beta-defensin 2 is a salt-sensitive peptide antibiotic expressed in human lung. J Clin Invest 1998; 102:874-80.

25. Tunzi C R, Harper P A, Bar-Oz B, Valore E V, Semple J L, Watson-MacDonell J, Ganz T, Ito S. Beta-defensin expression in human mammary gland epithelia. Pediatr Res 2000; 48:30-5.
26. Jia H P, Starner T. Ackermann M, Kirby P, Tack B F, McCray P B, Jr. Abundant human beta-defensin-1 expression in milk and mammary gland epithelium. J Pediatr 2001; 138:109-12.
27. Müller C A, Markovic-Lipkovski J, Klatt T, Gamper J, Schwarz G, Beck H, Deeg M, Kalbacher H, Widmann S, Wessels J T, Becker V, Muller G A, et al. Human alpha-defensins HNPs-1, -2, and -3 in renal cell carcinoma: influences on tumour cell proliferation. Am J Pathol 2002; 160:1311-24.
28. Mizukawa N, Sawaki K, Yamachika E, Fukunaga J, Ueno T, Takagi S, Sugahara T. Presence of human beta-defensin-2 in oral squamous cell carcinoma. Anticancer Res 2000; 20:2005-7.
29. Mizukawa N, Sawaki K, Nagatsuka H, Kamio M, Yamachika E, Fukunaga J, Ueno T, Takagi S, Sugahara T. Human alpha-and beta-defensin immunoreactivity in oral mucoepidermoid carcinomas. Anticancer Res 2001; 21:2171-4.
30. Sawaki K, Mizukawa N, Yamaai T, Yoslimoto T, Nakano M, Sugahara T. High concentration of beta-defensin-2 in oral squamous cell carcinoma. Anticancer Res 2002; 22:2103-7.
31. Jaynes J M, Julian G R, Jeffers G W, White K L, Enright F M. In vitro cytocidal effect of lytic peptides on several transformed mammalian cell lines. Pept Res 1989; 2:157-60.
32. Sharma S V. Melittin-induced hyperactivation of phospholipase A2 activity and calcium influx in ras-transformed cells. Oncogene 1993; 8:939-47.
33. Moore A J, Devine D A, Bibby M C. Preliminary experimental anticancer activity of cecropins. Pept Res 1994; 7:265-9.
34. Hui L, Leung K, Chen H M. The combined effects of antibacterial peptide cecropin A and anti-cancer agents on leukemia cells. Anticancer Res 2002; 22:2811-6.
35. Agerberth B, Charo J, Werr J, Olsson B, Idali F, Lindbom L, Kiessling R, Jörnvall H, Wigzell H, Gudmundsson G H. The human antimicrobial and chemotactic peptides LL-37 and alpha-defensins are expressed by specific lymphocyte and monocyte populations. Blood 2000; 96:3086-93.
36. Niyonsaba F, Iwabuchi K, Someya A, Hirata M, Matsuda H, Ogawa H, Nagaoka I. A cathelicidin family of human antibacterial peptide LL-37 induces mast cell chemotaxis. Immunology 2002; 106:20-6.
37. Tjabringa G S, Aarbiou J, Ninaber D K, Drijfhout J W, Sorensen O E, Borregaard N, Rabe K F, Hiemstra P S. The antimicrobial peptide LL-37 activates innate immunity at the airway epithelial surface by transactivation of the epidermal growth factor receptor. J Immunol 2003; 171:6690-6.

Example B

Increased Expression of hCAP18/LL-37 in Estrogen Receptor (ER) and Lymph Node (N) Positive Breast Tumours Materials and Methods RNA was extracted from 140 breast tumours and from 4 unaffected breast tissue samples and reverse transcribed using random hexamers as primers. The expression of hCAP18 transcripts was determined by real-time PCR using 10 ng of cDNA according to standard protocols (as described above).

Results and Discussion

Results are shown in FIG. 6. The mean expression of the unaffected samples was arbitrarily set to 1. Mean and deviation were evaluated by Anova statistics.

The expression of hCAP18 is significantly higher (by about 5 times) in ER positive tumors when lymph nodes have developed, than without lymph nodes.

Example C

Identification of Agents which Inhibit hCAP18/LL-37 Activity

A number of well-defined in vitro and in vivo assays can be used to demonstrate different aspects of the contribution of hCAP18/LL-37 to tumour development, namely the induction of well-known signal transduction pathways, the stimulation of cell proliferation and suppression of apoptosis, the stimulation of colony growth and anchorage independent growth, the stimulation of invasivity through a basement membrane, and finally, the enhanced tumour growth and metastasis formation in mice.

The above-mentioned characteristics, which have previously been attributed to hCAP18/LL-37 on primary keratinocytes and epithelial cell lines, can also be demonstrated on breast cancer cell lines. A suitable target cell line is MCF-7, a low malignant estrogen receptor positive cell line that does not express hCAP18. To investigate the aspects above, derivatives of MCF-7 are established that express hCAP18 from recombinant plasmids. Since the autocrine activity of hCAP18 protein and paracrine LL-37 will differ, the in vitro assays are also performed by exogenous addition of LL-37, if this is permitted by the nature of the experiment, instead of by endogenous production in the cell.

While the above experiments deal with evaluating the full tumourigenic potential of hCAP18/LL-37, further experiments can be performed to demonstrate the inhibition of these effects by agents with an anti-hCAP18/LL-37 activity. For example, the synthesized and active protein LL-37 can be considered as a target for inhibition by antibodies. Furthermore, the production of this protein can be hampered, by inhibiting the transcription of the hCAP18 gene via blocking of the promoter, as well as a posttranscriptional downregulation of the transcript by RNA interference.

Thus, experiments may be performed both in vitro, to demonstrate mechanism and target of action, and in vivo on tumours in the mouse, to demonstrate an effect in the body. Such in vitro experiments may be performed on the MCF-7 derivatives described above. For regulatory experiments on the hCAP18 gene, the breast cancer cell line ZR75-1 is used that expresses hCAP18 on a low but clearly detectable level.

For the experiments described below, the following conditions are used unless otherwise stated: cells are grown in Dulbecco's Modified Eagles medium containing 10% fetal calf serum. Medium for the transgenic lines contains 150 μg/ml Hygromycin and 400 μg/ml Geneticin to maintain the transgenes. For experiments lasting less than 3 days, the antibiotics are removed 24 h before use of the cells, and the fetal calf serum concentration is adjusted to the concentration necessary for each particular experiment. LL-37 is added at a concentration of 2 μM.

Stimulation of Cell Proliferation (see Heilborn 2005)

Transgenic cell lines and cell lines are harvested at 70% confluence and seeded at 2000 per well in 96-well plates in D/EM with 10% FCS. 24 h later, medium is changed to medium containing 5% FCS with or without addition of LL-37. After 24 h of culture, the cells are treated 12 h with 1 μCi/well of [3H]-thymidine, 20 Ci/mmol, and harvested (Harvester 96; Tomtec, Orage, Conn.) onto a glass fiber filter (Wallac, Turku, Finland). The incorporation of [3H]-thymidine is determined using a liquid scintillation counter (Microbeta Plus, Wallac). To ascertain statistic significance of the experiment, 24 wells are used for each condition/cell line.

Cell Growth Assay (see Lu 2005, Ludes-Meyers 2002)

This assay is performed as a complement to the [3H]-thymidine incorporation assay, to determine the stimulation of cell proliferation by hCAP18/LL-37. The MCF-7 derivatives are plated at a density of 50 cells/mm2 (approx. 50 000 cells/well in a 6 well plate) in triplicate for each time point. The total cell number is quantified every 2 days with a hematocytometer. Cell viability is assessed by using trypan blue.

Inhibition of Apoptosis by HCAP18/LL-37

For the induction of apoptosis, the cells are seeded at 25000 cells/well in 6 well plates medium with 5% FCS, and treated with the topoisomerase I inhibitor camptothecin (CAM) (Sigma Chemical Co., St. Luis, Mo.) at 6 μM for 24 h.

Two apoptotic parameters, DNA content and Caspase-3 activity, are evaluated to ascertain the repression of apoptosis by hCAP18/LL-37. All experiments are performed in setups of 6 to ascertain statistic significance.

Analysis of DNA Content by Flow Cytometry (see Warburton 2005)

The Propidium Iodide (PI)/RNase staining buffer (Becton Dickinson, San Jose, Calif.) is used for this analysis. Trypsinized cells are fixed in cold 70% (V/V) ethanol, and stored until its use at 4° C. The DNA content is measured through, incorporation of PI into DNA. Fluorometric analysis is performed using a FACScan flow cytometer (Becton and Dickinson, Mountain View, Calif., USA). FSC (forward light scatter) and SSC (side light scatter) of particles are simultaneously measured to determine the size and the granularity of cells. The red fluorescence of PI stained nuclei is detected in the FL-4 window (600 nm band pass filter and 35 nm band width). The intensity of fluorescence is proportional to the cellular DNA content. Each histogram is divided into two parts: (1) the M1 area representing asynchronous, non-apoptotic, live cells (cells in G1,S and G2 phases with DNA content equal to 2N to 4N); and (2) the M2 area representing apoptotic cells with a smaller quantity of DNA in comparison to living cells.

Caspase-3 Activity Assay

Caspase-3 enzymatic activity is measured using the fluorometric substrate VDVAD-AMC (100 μM) and DEVD-AMC (50 μM). Cell lysates are combined in a reaction buffer (100 mM HEPES, 10% sucrose, 5 mM dithiotlireitol (DTT), 10-6% NP-40, and 0.1% CHAPS, (pH 7.25) and added to a microtiter plate. The cleavage of the fluorogenic substrate is monitored by AMC liberation in a Fluoroscan II plate reader (Labsystems, Stockholm, Sweden). Fluorescence units are converted to pmol of AMC using a standard curve generated from free AMC. Data are analyzed by linear regression.

Colony Formation Assay (see Ludes-Meyers 2002, Wang 2005)

This assay is used to determine the capacity of a cell for sustained proliferation in absence of supporting, neighbouring cells. This property is considered to reflect the capacity of the cell to form tumours.

The transgenic cells are maintained under subconfluent conditions and trypsinized at 70% confluency at max, and are then diluted to a concentration of 5, 10, and 25 cells/ml growth medium. Cells are grown for 3 to 7 days (principally sufficient for 3 to 4 doublings), and the number of cells per colony is determined. If the recombinant plasmid expresses green fluorescent protein, cells and colonies can be counted in a fluorescence microscope. The result of colony formation is expressed as a distribution of fluorescent cells per colony, and a Wilcoxon's rank-sum test is used to compare distributions between the different transgenic lines, in presence and absence of LL-37 in the medium. Since MCF-7 cells are known to form tumours in presence of β-estrogen only, the effect of 1-5 nM estrogen to the growth of the transgenic cells can be assayed.

Assay for Anchorage Independent Growth (see Fiucci 2002)

This assay reflects the capacity of the cell to form metastases. Cells are prepared by treatment with a mixture of 300 u/ml trypsin, 20 u/ml elastase, and 1 mM EDTA. The presence of elastase facilitates the dissociation of cells into single cell suspensions. Cells are suspended in growth medium and mixed 1:1 with growth medium containing molten 0.7% Seaplaque low melting temperature agarose, at a final concentration of 500 cells/ml and 0.35% agarose. 1 ml of this mix are plated in 6 well plates, over a 2 ml layer of solidified medium/0.6% agarose. The cells are fed every 3-4 days be adding 100 μl of growth medium. After 2 weeks the top layer of the culture is stained with 0.2% p-iodonitrotetrazoliium violet (Sigma), and colonies larger than 100 μM in diameter are counted. The assay is performed in triplicates, and repeated twice.

Induction of Invasivity (see Fiucci 2002)

Matrigel is considered as basement membrane and generated from EHS sarcoma. Matrigel contains not only basement membrane components (collagens, laminin, and proteoglycans) but also matrix degrading enzymes/their inhibitors and growth factors. Invasion of tumour cells into Matrigel has been used to characterize the involvement of extracellular matrix receptors and matrix degrading enzymes which play roles in tumour progression.

Matrigel is diluted to 2 mg/ml in serum free cold growth medium, and 100 μl are placed into the upper chamber of a 24-well transwell and incubated at 37° C. over night for gelling. Cells are harvested and resuspended in medium containing 1% FCS at a density of 106/ml. After washing the matrigel with worm serum free medium, 100 μl of the cell suspension is placed on top. The lower chamber is filled with 600 μl of growth medium containing conditioned medium as chemoattractant. The chambers are incubated in the cell incubator for 6 h to 24 h. The transwells are stained (Diff-Quick staining solution, Fisher Scientific) and, after scraping off the noninvaded cells with a cotton swab, the invaded cells are counted in a light microscope.

Tumour Growth in SCID Mice (see Wang 2005 Warburton 2005)

Subconfluently grown cells are harvested and suspended in cold PBS at 2.5×107 cells/ml. 200 μl portions are injected subcutaneously, into the fat pad, or into the tail vein of 4-6 week old female SCID mice. Since the tumour formation of MCF-7 cells generally depends on estrogen, pellets have been implanted subcutaneous to release 1.7 mg β-estradiol per day over 60 days. The mice are palpated twice per week and the date when the first palpable tumour arises is recorded. Tumour growth is monitored manually, and mice are sacrificed latest at a tumour diameter of 1 cm. The number, size and distribution of tumours is recorded. Small metastases are detected by sectioning the mice, and scanned to induce fluorescence from the GFP expressed from the recombinant plasmids. In addition, spleen and liver are collagenized, and single cell suspensions are evaluated in a FACS sorter to determine the number of fluorescent cells.

Inhibitory Studies Smith Antagonists to hCAP18 Transcription (see Agarwal 1998, Andela 2004, Toell 2001, Ishizuka 2005, Weber 2005)

The strongest inducer of hCAP18 transcription presently known is vitamin D. The vitamin D receptor directly activates hCAP18 transcription by binding to a response element in the HCAP18 promoter. Since thus small molecules can control the expression of hCAP18, it is meaningful to systematically screen for inhibitory compounds. Initial studies have shown that estrogen and some of its metabolites have no effect. Vitamin A inhibits the transcription in skin keratinocytes but stimulates transcription in the breast cancer cell line ZR-75-1. Based on these findings, antagonists to vitamin D, such as ZK159222 (Schering A G), and TEI-9647 (Tejin Institute for Medical Research, Tokyo), and antagonists to vitamin A such as AGN193109 (Allergen Pharmaceuticals), are potential agents for use in the methods of the invention.

Screening of Inhibitors of hCAP18 Transcription (see Weber 2005)

ZR75-1 cells are plated at 25% confluency and treated with the potential inhibitor, dissolved in isopropanol or DMSO at 100 μM, at a final concentration of 100 nM. After 24 h, RNA is extracted with the Qiagen RNeasy kit (Operon Biotechnologies, Cologne, Germany) and reverse transcribed with a first strand synthesis kit (Amersham Biosciences, Norwalk, Conn.). RNA is quantified by Real-Time PCR on an ABI Prism 7700 (Applied Biosystems) using 5 ng of cDNA according to standard protocols. The samples are evaluated in triplicates. Sequences are 5'-GTCACCAGAGGATTGT-GACTTCAA-3' [SEQ ID NO: 2] and 5'-TTGAGGGTCACT-GTCCCCATA-3' [SEQ ID NO: 3] for the primers, and 6-FAM-5'-CCGCTTCACCAGCCCGTCCTT-3'-BHQ1 [SEQ ID NO: 4] for the fluorigenic probe. The samples are normalized by quantification of 18S-RNA (Assay on Demand, Applied Biosystems).

To investigate the regulatory mechanism of the inhibition, the activity of the promoter is determined by use of a recombinant plasmid in which the hCAP18 promoter controls a luciferase reporter genie. ZR75-1 cells are plated at 25% confluency in 6-well plates, and transfected per well with 3 μg the reporter plasmid complexed with 6 μl of jetPEI (qBiogene). 14 h past transfection, the inhibitor is added as above. 24 h later, the cells are lysed and luciferase activity is measured in assay systems (Promega). The activities are normalized against β-galactosidase, expressed from 200 ng of cotransfected plasmid (pEF1/lacZ, Invitrogen). Each experiment is performed at least twice and in triplicates in each assay.

Posttranscriptional Inhibition Studies (see Wang 2005, Zhang 2005, Roh 2000)

Today's most effective posttranscriptional inhibition is RNA interference, which basically induces a sequence specific and catalytic degradation of the target mRNA. The most effective target sites in a transcript can most easily be screened in a cell line into which short interfering RNA is transfected. The efficiency of RNA interference is monitored by quantitative PCR and Western blot analysis. A successful target site can then be expressed in a recombinant vector, designed to express the target molecule at the site of the tumour.

A short interfering RNA is designed and synthesized on basis of the coding sequence of hCAP18. This RNA consists of a double-stranded 19-mer, plus a 2-base dTdT-overhang on either side. For the design commercial siRNA databases can most simply be used in which target sites have been preselected (for hCAP18 e.g. siRNAs no. 14586, 14402, 146365 from Ambion). ZR75-1 cells or transgenic MCF-7 cells are transfected with siRNA at a final concentration of 10 nM at max. to avoid an unspecific response, such as interferon-related pathways. Control siRNA contains 2-3 mismatches in the target sequence. Cells are harvested 24-72 h after transfection, and the expression of hCAP18 is determined by Real-Time PCR as described above, and by quantitative Western blot analysis. For Western blot analysis, protein is extracted in SDS-containing sample buffer, separated on a 15% Tris-Glycine gel and electroblotted onto nitrocellulose filters as described above. Filters are reversibly stained with 3% Ponceau S before incubating with affinity purified anti-LL-37 antiserum at 1/1000 dilution. Signals from HRP-conjugated secondary IgG using enhanced chemoluminiscence are captured and evaluated as described above.

The in vivo experiment is set up for the most effective transcriptional inhibitor of hCAP18 expression. 12 mice are injected with MCF-7 cells expressing transgenic hCAP 18. Half of the mice receive daily subcutaneous injections of 30 mg inhibitor, dissolved in 50 μl olive oil (Sigma). The onset of tumour formation, size and distribution is assayed as above. siRNA valid for in vivo approaches should downregulate hCAP18 expression by at least 90%.

For interfering with tumour formation in the mouse, the downregulation of hCAP18 expression needs to be maintained for several weeks. Daily injections of high amounts of siRNA into the tail vein have been proven possible but appear little realistic for therapeutic approaches. The alternative is a stable expression of siRNA in the organism/tumour cell. Plasmids have been designed (e.g. pSuper, OriGene Inc) that express RNA as a hairpin, which then is intracellularly converted into siRNA. For our initial approach, the target siRNA sequence determined by above experiments is cloned into pSuper, and tumour cells are transfected with this construct prior to implantation into the mouse. Therapeutic approaches, i.e. the delivery of expression vectors past tumour formation, are presently not yet developed, but the delivery of plasmid with liposomes and the construction of retroviral and adenoviral expression vectors for this purpose is investigated worldwide.

An alternative to RNAi is the "classical" antisense approach. Single-stranded oligonucleotides of 20-3 bp in length, complementary to the target transcript are directly added into the cell medium or injected into the mouse. The backbone of the oligonucleotide is usually modified, to inhibit its degradation and to facilitate its uptake without any carrier substrates. However, the method require a high dosage since the inhibitory mechanism is noncatalytic, and the backbone modifications increase the cytotoxicity and inspecific side effects. In mouse experiments, a typical administration range is 100-500 μg/animal/day.

Inhibition of LL-37 Activity with Antibodies (see Warburton 2005)

Chicken antibodies have been produced and affinity purified in large scale, sufficient for the planned experiments. Antibodies against LL-37 have previously been shown capable to inhibit the activity of LL-37. In vitro experiments are therefore not required.

For in vivo experiments, tumours are induced in the mouse as above. Antibodies are injected twice weekly when tumours are palpable, using 1-100 mg/kg antibody at the beginning.

The effect of the antibody on tumour development is then assessed.

References

1. Agarwal C et al.: AGN193109 is a highly effective antagonist of retinoid action in human ectocervical epithelial cells. J Biol Chem 271: 12209-12212 (1996).
2. Andela V B, Rosier R N: The proteosome inhibitor MGI32 attenuates retinoic acid receptor trans-activation and enhances trans-repression of nuclear factor B. Potential relevance to chemo-preventive interventions with retinoids. Molecular Cancer 3: 8-19 (2004).
3. Fiucci G, Ravid D, Reich R, Liscovitch M: Caveolin-1 inhibits anchorage-independent growth, anoikis and invasiveness in MCF-7 human breast cancer cells. Oncogene 21: 2365-2375 (2002).
4. Heilborn J et al.: Antimicrobial protein hCAP18/LL-37 is highly expressed in breast cancer and is a putative growth factor for epithelial cells. Int J Cancer 114:713-9 (2005).
5. Ishizuka S et al.: (23S)-25-Dehydro-1{alpha}-hydroxyvitamin D3-26,23-lactone, a vitamin D receptor antagonist that inhibits osteoclast formation and bone resorption in bone marrow cultures from patients with Paget's disease. Endocrinology. 146:2023-2030 (2005).
6. Lu C, Shen Q et al.: cFos is critical for MCF-7 breast cancer cell growth. Oncogene 24: 6516-6524 (2005).
7. Ludes-Meyers J H et al.: AP-1 blockade inhibits the growth of normal and malignant breast cells. Oncogene 20: 2771-2780 (2001).
8. Roh H et al.: HER2/neu antisense targeting of human breast carcinoma. Oncogene. 2000 Dec. 11; 19(53):6138-43.
9. Toell A et al.: Different molecular mechanisms of vitamin D3 receptor antagonists. Mol Pharmacol 59: 1478-1485 (2001).
10. Wang Y-h et al.: Knockdown of c-Myc expression by RNAi inhibits MCF-7 breast tumour cells growth in vitro and in vivo. Breast Cancer Res 7: R220-R228 (2005).
11. Warburton C et al.: Treatment of HER-2/neu overexpressing breast cancer xenograft models with trastuzumab (Herceptin) and gefitinib (ZD1839): drug combination effects on tumour growth, HER-2/neu and epidermal growth factor receptor expression, and viable hypoxic cell fraction. Clin Cancer Res. 10:2512-24 (2004).
12. Weber G et al.: Vitamin D induces the antimicrobial protein hCAP18 in human skin. J Invest Dermatol. 124: 1080-2 (2005).
13. Zhang M et al.: Silencing the epidermal growth factor receptor gene with RNAi may be developed as a potential therapy for non small cell lung cancer. Genet Vaccines Ther. 3:5-16 (2005).

Example D

The Human Antimicrobial Peptide LL-37 Inhibits Apoptosis and Upregulates the Expression of the Inhibitor of Apoptosis Protein (IAP-2) in Cultured Human Keratinocytes Introduction Cathelicidins are a family of antimicrobial peptides found in many mammalian species. They consist of a highly conserved amino-terminal domain, cathelin, and a variable carboxy-terminal domain which is released by proteolysis to confer the antimicrobial activity.(1,2). The only human member of this family, 18 kDa human cationic antimicrobial protein (hCAP18), is produced mainly by neutrophils, several epithelial and mucosal cells (skin, bronchi, buccal mucosa, sophagous, cervix, vagina, epidimus and salivary glands) (3-8). The C-terminal 37 amino acid domain, LL-37 displays antimicrobial activity against a broad spectrum of microorganisms (9,10) through disruption of the membrane stability (11,12).

Beyond the antimicrobial functions, this peptide has been implicated in other biological activities, such as chemotaxis and cytokine release (8,13) in blood and epithelial cells, induction of epithelial cell proliferation (14) and angiogenesis (15). Recent studies have shown that LL-37 is highly expressed during wound healing, affects the in vitro proliferation of human keratinocytes and is involved in re-epithelization of wounds (16,17).

Materials and Methods

Cell Cultures

Foreskin Epidermal keratinocytes were obtained from Cascade Biologics (Cascade Biologics, Eugene, Oreg.) and cultured in Epilife basal Medium (Cascade Biologics.) supplemented with 0,06 mM Calcium, 0.2% v/v BPE, 5 µg/ml bovine insuline, 0.18 µg/ml hydrocortisone, 5 µg/ml bovine transferrin, 0.2 µg/ml human epidermal growth factor, 100 U/ml penicillin G, 100 µg/ml streptomycin sulfate, and 0.25 µg/ml Ampotericin B (all Cascade Biologics) at 37° C. and 5% CO2. Cells were passaged weekly using 0.025% (w/v) trypsin and 0.01% (w/v) EDTA (Cascade Biologics).

HaCaT keratinocytes were cultivated in DMEM (Dulbecco's modified Eagle's Medium; Gibco-BRL Technology, Paisley, UK) supplemented with 10% foetal calf serum (hyClone, Boule Nordic AB Huddinge, Sweden), 2 mM glutamine, penicillin (50 U/L Gibco-BRL) and streptomycin (50 mg/ml, Gibco-BRL).

Cell Treatment 25,000 cells/well were plated in 6-well plate culture dishes. 48 after plating, cells were treated with 0, 0.23, 0.46, 0.69, 0.9, 1.15, 2.3, 4.6 and 11.5 µM LL-37. Each treatment was performed in triplicate. The peptide was diluted in medium (DMEM 5% FCS to HaCaT cells and Epilife basal Medium supplemented with 0.1% FCS to HEKn cells). The cells were treated during a total time of 24 h. After LL-37 stimulation, the topoisomerase I inhibitor camptothecin (CAM) (Sigma Chemical Co., St. Luis, Mo.) in dimethylsulfoxide was added to the cells to a final 6 µM concentration. Cells were further incubated for 24 h before analysis.

Evaluation of Apoptosis by Flow Cytometry

Two apoptotic parameters, the loss of the membrane integrity and DNA decrease were evaluated by flow cytometry.

Evaluation of Membrane integrity: After stimulation with LL-37, and treatment with CAM, cells were harvested by trypsinization. The cells were then washed in cold Dulbecco's phosphate-buffered saline (PBS) and counted with a haemocytometer (Hausser Scientific, Horsham, Pa.). Cell density was adjusted to $1 \times 10^6$ cells/ml in PBS. Apoptosis was detected by staining with propidium iodide and YO-PRO-1 dye (Molecular Probes, Eugene, Oreg.). Stained cells were analyzed on a FACScan (Beckton-Dickinson, San Jose, Calif.). Cells were gated for analysis on the basis of the forward (FSC) and side light scatter characteristics (SSC). Analysis of cells expressing YO-PRO and propidium iodide (PI) was done using Cell Quest software (Becton Dickinson), which provided percentages of YO-PRO and PI-positive cells. Cells that stained green with YO-PRO were considered apoptotic. Cells that stained also red, with propidium iodide, were necrotic. Live, viable cells take up little or no dye.

Analysis of DNA content by flow cytometry. The PI/RNase staining buffer (BectonDickinson) was used for this analysis. Trypsinized cells were fixed in cold 70% (v/v) ethanol, and stored until its use at 4° C. The DNA content was measured through incorporation of propidium iodide into DNA. Fluorometric analysis was performed using a FACScan flow cytometer (Becton and Dickinson, Mountain View, Calif., USA). FSC (forward light scatter) and SSC (side light scatter) of particles were simultaneously measured to determine the size and the granularity of cells. The red fluorescence of PI stained nuclei was detected in the FL-4 window (600 nm band pass filter and 35 nm bandwidth). The intensity of fluorescence was proportional to the cellular DNA content. Each histogram was divided into two parts: (1) the M1 area representing asynchronous, non-apoptotic, live cells (cells in G1,S and G2 phases with DNA content equal to 2n to 4N); and (2) the M2 area representing apoptotic cells with a smaller quantity of DNA in comparison to living cells.

Caspase-3 Activity Assay

Caspase-3 enzymatic activity was estimated using the fluorometric substrate VDVAD-AMC (100 µM) and DEVD-AMC (50 µM) as previously described. Briefly, cell lysates were combined in a reaction buffer (100 mM HEPES, 10% sucrose, 5 mM dithiothreitol (DTT), 10-6% NP-40, and 0.1% CHAPS, (pH 7.25) and added to a microtiter plate. The cleavage of the fluorogenic substrate was monitored by AMC liberation in a Fluoroscan II plate reader (Labsystems, Stockholm, Sweden). Fluorescence units were-converted to pmol of AMC using a standard curve generated from free AMC. Data were analyzed by linear regression and are displayed as pmol AMC release per min.

RT-PCR

Total RNA was isolated from cells after different treatments according to the manufacturer's directions by using the Quiagen RNasy kit (Operon Biotechnologies, Cologne, Germany). Reverse transcription was performed with a first-strand synthesis kit (Amershan Biosciences)

Results

Inhibition of CAM induced apoptosis by LL-37

We examined the effect of LL-37 on cell death and apoptosis induced by CAM, a drug widely used as an apoptosis-inducing agent. After treatment, membrane integrity and DNA fragmentation were analyzed by flow cytometry using two methods. The first method was a two-stain system that allows us to distinguish increased cell membrane permeability; the untreated cells were analyzed for staining intensity (FIG. 7) and categorized in three types: viable non-stained cells, apoptotic YO-PRO stained cells and necrotic cells stained both by YO-PRO and PI. In the second method the DNA content in ethanol permeabilised cells was analysed by PI. Apoptotic cells shown less amount of DNA due to fragmentation.

Concentration and time point experiments were performed before in order to choose a dose and time that induced apoptosis in HaCaT and HEKn cells (data not shown). When exposed to 6 µM of CAM during 24 hours both HaCaT and keratinocytes exhibited morphological changes characteristic of apoptosis such as alterations in membrane integrity and DNA profile. (FIG. 7). When the cells were treated for 24 h with LL-37 alone or simultaneously with LL-37 and CAM, not change in the amount of apoptotic cells was observed (data not shown). However, high concentrations of LL-37 (4.6 and 11.5 µM) were cytotoxic, leading to an increased fraction of necrotic but not of apoptotic cells. The results were different when, instead of simultaneous treatment, the cells were exposed to LL-37 for 24 hours before apoptosis induction by CAM. At concentrations from 0.23 µM and up to 2,3 µM LL-37 inhibited both DNA fragmentation and loss of membrane permeability in HEKn and HaCaT cells (FIGS. 7 and 8). Also under these conditions, LL-37 caused cell death at higher concentrations (4.6 µM and 11.5 µM). Even at toxic concentration the fraction of apoptotic cells remained low, indicating that cell death by LL-37 occurred by non-apoptotic mechanisms.

LL-37 Inhibits the Induction of Caspase-3 by CAM in HaCaT and HEKn Cells

Since caspase-3 is one of the key proteins in the apoptosis pathway and it is an early indicator of apoptosis, we decided to measure caspase-3 activity in keratinocytes treated with or without LL-37. Caspase activity was significantly increased in keratinocytes within the first 12 hours of CAM treatment and peaked at 24 hours. Pre-treatment with 2.3 µM of LL-37 decreased camptothencin-induced caspase activation (FIGS. 9a and b). These data suggest that LL-37 inhibits apoptosis in human keratinocytes by diminishing caspase activity.

LL-37 induces IAP-2 Expression in Human Keratinocytes

Members of the inhibitor of apoptosis proteins (IAP) have been described as key regulators of apoptosis. This family has the ability to inhibit the activity of caspase-3. The antiapoptotic functions of the porcine cathelicidin member PR39 has been related with the induction of IAP-2 expression. Therefore we analyzed by RT-PCR the expression in HEKn cells of IAP-2 in keratinocytes treated wit different concentrations of LL-37 and at different time points. Stimulation with 2.3 µM LL-37 increased IAP-2 mRNA from 6 hours and to 12 hours after stimulation (FIG. 10). Concentrations of LL-37 below to 2.3 µM did not affect the c-IAP-2 levels (data not shown)

Keratinocytes Stimulated with LL-37 Up-regulate COX-2

Previous studies had identified COX-2 as a regulator of IAP-2 expression, since ihhibition of COX-2 in epithelial cells decreased the expression of IAP-2. We therefore analyzed the expression of COX-2 in HEKn treated with 2.3 µM of LL37. A time-dependent increase in mRNA levels was found (FIG. 11) with the highest levels evident after 12 hours. To assay whether COX-2 is mediating the IAP-2 increased expression after LL-37 stimulation, HEKn cells were pre-treated for 12 h with 25 nM of the specific COX-2 inhibitor SC-791, and then stimulated with 2 µM LL-37. Under these conditions LL-37 treatment did not increase the IAP-2 mRNA levels as was observed previously. (FIG. 12) These data suggest that LL-37 increases the IAP-2 levels trough the increase in the expression of the COX-2 enzyme.

Discussion

Increased expression of the antimicrobial peptide LL-37 had been reported followed to cutaneous injury. The expression of this peptide has been associated with promotion of wound healing not only trough the prevention of infection but also through the active participation on different wound healing-related processes such as chemotaxis, migration, angiogenesis and re-epithelization.

The present data show that LL-37 is also involved in promoting cell survival in keratinocytes via an inhibitory effect on apoptosis.

Abbreviations hCAP18/LL-37, human cathelicidin antimicrobial peptide 18 kDa/LL-37; IAP-2, Inhibitor apoptosis protein-2; COX-2, ciclooxygenase-2; VDVAD-AMC, caspase 3 substrate; HEKn, human epidermal keratinocytes neonatal; DMEN, Dulbecco's Modified Eagle's Medium; PBS, phosphate buffered saline. DEVDase, Asp-Glu-Val-Asp protease activities CHAPS, 3-[(3-cholamidopropyl)dimethyl-ammmonio] propane-1-sulphonic acid, CAM: Camptothecin References 1. Zanetti, M., Gennaro, R., and Romeo, D. (1995) *FEBS Lett* 374(1), 1-5
2. Sorensen, O. E., Follin, P., Johnsen, A. H., Calafat, J., Tjabringa, G. S., Hiemstra, P. S., and Borregaard, N. (2001) *Blood* 97(12), 3951-3959

3. Sorensen, O., Arnljots, K., Cowland, J. B., Bainton, D. F., and Borregaard, N. (1997) *Blood* 90(7), 2796-2803
4. Bals, R., Wang, X., Zasloff, M., and Wilson, J. M. (1998) *Proc Natl Acad Sci USA* 95(16), 9541-9546
5. Frohm, M., Agerberth, B., Ahangari, G., Stahle-Backdahl, M., Liden, S., Wigzell, H., and Gudmundsson, G. H. (1997) *J Biol Chem.* 272(24), 15258-15263
6. Agerberth, B., Gunne, H., Odeberg, J., Kogner, P., Boman, H. G., and Gudmundsson, G. H. (1995) *Proc Natl Acad Sci USA* 92(1), 195-199
7. Frohm Nilsson, M., Sandstedt, B., Sorensen, O., Weber, G., Borregaard, N., and Stahle-Backdahl, M. (1999) *Infect Immun* 67(5), 2561-2566
8. De, Y., Chen, Q., Schmidt, A. P., Anderson, G. M., Wang, J. M., Wooters, J., Oppenheim, J. J., and Chertov, O. (2000) *J Exp Med* 192(7), 1069-1074
9. Zasloff, M. (2002) *Nature* 415(6870), 389-395
10. Dorschner, R. A., Pestonjamasp, V. K., Tamakuwala, S., Ohtake, T., Rudisill, J., Nizet, V., Agerberth, B., Gudmundsson, G. H., and Gallo, R. L. (2001) *J Invest Dermatol* 117(1), 91-97
11. Oren, Z., Lerman, J. C., Gudmundsson, G. H., Agerberth, B., and Shai, Y. (1999) *Biochem J* 341 (Pt 3), 501-513
12. Ramanathan, B., Davis, E. G., Ross, C. R., and Blecha, F. (2002) *Microbes Infect* 4(3), 361-372
13. Braff, M. H., Hawkins, M. A., Di Nardo, A., Lopez-Garcia, B., Howell, M. D., Wong, C., Lin, K., Streib, J. E., Dorschner, R., Leung, D. Y., and Gallo, R. L. (2005) *J Immunol* 174(7), 4271-4278
14. Shaykhiev, R., Beisswenger, C., Kandler, K., Senske, J., Puchner, A., Damm, T., Behr, J., and Bals, R. (2005) *Am J Physiol Lung Cell Mol Physiol* 289(5), L842-L848
15. Koczulla, R., von Degenfeld, G., Kupatt, C., Krotz, F., Zahler, S., Gloe, T., Issbrucker, K., Unterberger, P., Zaiou, M., Lebherz, C., Karl, A., Raake, P., Pfosser, A., Boekstegers, P., Welsch, U., Hiemstra, P. S., Vogelmeier, C., Gallo, R. L., Clauss, M., and Bals, R. (2003) *J Clin Invest* 111(11), 1665-1672
16. Heilborn, J. D., Nilsson, M. F., Jimenez, C. I., Sandstedt, B., Borregaard, N., Tham, E., Sorensen, O. E., Weber, G., and Stahle, M. (2005) *Int J Cancer* 114(5), 713-719
17. Heilborn, J. D., Nilsson, M. F., Kratz, G., Weber, G., Sorensen, O., Borregaard, N., and Stahle-Backdahl, M. (2003) *J Invest Dermatol* 120(3), 379-389

Example E

Production and Use in vivo of Targeted Agents of the Invention

Expression of Anti-hCAP18/LL-37 Antibody/Anti-HMFG1 Antibody Fusion

A fusion protein comprising an inhibitor portion (anti-hCAP18/LL-37 antibody) and a targeting portion (anti-polymorphic epithelial mucin antibody, HMFG1) is expressed in NSO myeloma cells.

In brief, NSO myeloma cells are co-transfected by electroporation with expression vectors encoding the constituent light and heavy chains of the fusion protein. Transfectomas are then selected and screened for antibody production by ELISA assays.

Administration to Patients

The fusion protein is formulated into an aqueous sterile injection solution.

The formulation is then administered into patients suffering from breast cancer by intravenous (IV) infusion over 90 minutes.

The dose is selected according to the individual requirements of each patient, as determined by the medical practitioner. Typically, however, an initial dose of 4 mg/kg is used followed by weekly maintenance doses of 2 mg/kg.

Monitoring Disease Progression

The impact of treatment with the fusion protein on the progression of the breast cancer is then monitored by conventional mammography.

The invention claimed is:

1. A method for inhibiting the proliferation of cancer cells in a patient, the method comprising administering to the patient a polypeptide which inhibits hCAP18/LL-37 by inhibiting the binding properties of hCAP18/LL-37, wherein the cancer cells are breast cancer cells.

2. The method according to claim 1 wherein the patient is human.

3. The method according to claim 1 or 2 wherein the polypeptide is selectively delivered to or selectively activated by the cancer cells.

4. The method according to claim 1 wherein the breast cancer cells are Elston grade III cells.

5. The method according to claim 4 wherein the breast cancer cells are metastatic.

6. The method according to claim 1 wherein the polypeptide is an antibody or an antigen-binding fragment thereof.

7. The method according to claim 6 wherein the antigen-binding fragment is selected from the group consisting of Fv fragments, Fab-like fragments, single variable domains and domain antibodies.

* * * * *

SEQUENCE LISTING

<160> NUMBER OF SEQ ID NOS: 4

<210> SEQ ID NO 1
<211> LENGTH: 739
<212> TYPE: DNA
<213> ORGANISM: Unknown
<220> FEATURE:
<223> OTHER INFORMATION: HCAP18/LL-37

<400> SEQUENCE: 1

```
taaagcaaac cccagcccac accctggcag gcagccaggg atgggtggat caggaaggct      60
cctggttggg cttttgcatc aggctcaggc tgggcataaa ggaggctcct gtgggctaga     120
gggaggcaga catggggacc atgaagaccc aaagggatgg ccactccctg gggcggtggt     180
cactggtgct cctgctgctg ggcctggtga tgcctctggc catcattgcc caggtcctca    240
gctacaagga agctgtgctt cgtgctatag atggcatcaa ccagcggtcc tcggatgcta    300
acctctaccg cctcctggac ctggacccca ggcccacgat ggatggggac ccagacacgc    360
caaagcctgt gagcttcaca gtgaaggaga cagtgtgccc caggacgaca cagcagtcac    420
cagaggattg tgacttcaag aaggacgggc tggtgaagcg gtgtatgggg acagtgaccc    480
```

```
tcaaccaggc caggggctcc tttgacatca gttgtgataa ggataacaag agatttgccc      540
tgctgggtga tttcttccgg aaatctaaag agaagattgg caaagagttt aaaagaattg      600
tccagagaat caaggatttt ttgcggaatc ttgtacccag gacagagtcc tagtgtgtgc      660
cctaccctgg ctcaggcttc tgggctctga gaaataaact atgagagcaa tttcaaaaaa      720
aaaaaaaaaa aaaaaaaa                                                    739

<210> SEQ ID NO 2
<211> LENGTH: 24
<212> TYPE: DNA
<213> ORGANISM: Artificial Sequence
<220> FEATURE:
<223> OTHER INFORMATION: hCAP18 qRT-PCR synthetic primer 1

<400> SEQUENCE: 2
gtcaccagag gattgtgact tcaa                                              24

<210> SEQ ID NO 3
<211> LENGTH: 21
<212> TYPE: DNA
<213> ORGANISM: Artificial Sequence
<220> FEATURE:
<223> OTHER INFORMATION: hCAP18 qRT-PCR synthetic primer 2

<400> SEQUENCE: 3
ttgagggtca ctgtccccat a                                                 21

<210> SEQ ID NO 4
<211> LENGTH: 21
<212> TYPE: DNA
<213> ORGANISM: Artificial Sequence
<220> FEATURE:
<223> OTHER INFORMATION: hCAP18 fluorigenic synthetic probe
<220> FEATURE:
<221> NAME/KEY: misc_feature
<222> LOCATION: (1)...(1)
<223> OTHER INFORMATION: 5' 6-Carboxyfluorescein
<220> FEATURE:
<221> NAME/KEY: misc_feature
<222> LOCATION: (21)...(21)
<223> OTHER INFORMATION: 3' BHQ1 quencher molecule

<400> SEQUENCE: 4
ccgcttcacc agcccgtcct t                                                 21
```